(12) United States Patent
Borillo et al.

(10) Patent No.: US 12,274,819 B2
(45) Date of Patent: *Apr. 15, 2025

(54) HEMODIALYSIS SYSTEM WITH VARIABLE DIALYSATE FLOW RATE

(71) Applicant: DIALITY INC., Irvine, CA (US)

(72) Inventors: Brandon Borillo, Irvine, CA (US); Tzu Tung Chen, Irvine, CA (US); Clayton Poppe, Irvine, CA (US)

(73) Assignee: Diality Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/410,800

(22) Filed: Jan. 11, 2024

(65) Prior Publication Data

US 2024/0307595 A1    Sep. 19, 2024

Related U.S. Application Data

(63) Continuation of application No. 17/334,393, filed on May 28, 2021, now Pat. No. 11,904,078.

(51) Int. Cl.
| | |
|---|---|
| *A61M 1/16* | (2006.01) |
| *A61M 1/38* | (2006.01) |
| *B01D 46/00* | (2022.01) |

(52) U.S. Cl.
CPC ........ *A61M 1/1647* (2014.02); *A61M 1/1672* (2014.02); *A61M 1/38* (2013.01); *B01D 46/0036* (2013.01); *A61M 2205/3334* (2013.01)

(58) Field of Classification Search
CPC ...... A61M 37/00; A61M 37/01; A61M 37/16; A61M 37/3621; A61M 37/3639;
(Continued)

(56) References Cited

U.S. PATENT DOCUMENTS

| | | |
|---|---|---|
| 6,602,424 B1 | 8/2003 | Kramer et al. |
| 10,220,132 B2 | 3/2019 | Patel et al. |
| | (Continued) | |

FOREIGN PATENT DOCUMENTS

| | | |
|---|---|---|
| WO | WO 2004/082733 A2 | 9/2004 |
| WO | WO 2012/148781 A1 | 11/2012 |

OTHER PUBLICATIONS

EP, EP 22193288.2 Extended European Search Report, Feb. 6, 2023.
WO, PCT/US2024/040434 International Search Report, Oct. 28, 2004.

*Primary Examiner* — Akash K Varma
(74) *Attorney, Agent, or Firm* — One LLP

(57) ABSTRACT

A portable hemodialysis system is provided including a dialyzer, a closed loop blood flow path which transports blood from a patient through the dialyzer and back to the patient, and a closed loop dialysate flow path which transports dialysate through the dialyzer. Preferably, the hemodialysis system includes a sorbent filter in the dialysate flow path. Furthermore, the hemodialysis machine includes a blood pump, and a pair of dialysate pumps. A processor controls the flow of blood through the blood flow path, and the processor controls the flow of dialysate through the dialysate flow path. In addition, the processor stores a patient treatment plan wherein the flow rate of dialysate reduces throughout treatment to maximize the amount of urea removed by the sorbent filter.

12 Claims, 13 Drawing Sheets

(58) Field of Classification Search
CPC ...... A61M 2205/125; A61M 2205/126; A61M 2205/127; A61M 2205/15; A61M 2205/27; A61M 2205/33; A61M 2205/3303; A61M 2205/3306; A61M 2205/3327; A61M 2205/3334; A61M 2205/3337; A61M 2205/3368; A61M 2205/3379; A61M 2205/3653; A61M 2205/50; A61M 2205/75; A61M 2205/52; A61M 1/10; A61M 1/14; A61M 1/16; A61M 1/34; A61M 1/341; A61M 1/1654; A61M 1/1656; A61M 1/1658; A61M 1/1647; A61M 1/1601; A61M 1/3403; A61M 1/1605; A61M 1/1603; A61M 1/1609; A61M 1/1621; A61M 1/1645; A61M 1/1672; A61M 1/267; A61M 1/3661; A61M 1/1696; A61M 1/3626; A61M 1/38; A61M 1/1607; A61M 1/1613; A61M 1/3652; A61M 1/3612; A61M 1/1615; B01D 46/0036; B01D 46/00; B01D 61/42; G01F 1/075; G01F 1/0755; G01F 1/115; G01F 1/1155; G01F 1/58

USPC ............................................ 210/85, 86, 646
See application file for complete search history.

(56) References Cited

U.S. PATENT DOCUMENTS

| | | |
|---|---|---|
| 10,258,728 B2 | 4/2019 | Gerber |
| 10,449,285 B2 | 10/2019 | Chamney et al. |
| 10,532,146 B2 | 1/2020 | Jirka et al. |
| 2007/0066928 A1* | 3/2007 | Lannoy ............... A61M 1/3612 604/6.07 |
| 2011/0009797 A1* | 1/2011 | Kelly ................. A61M 1/3652 604/6.11 |
| 2019/0117866 A1 | 4/2019 | Giordano et al. |
| 2020/0330668 A1 | 10/2020 | Maierhofer |
| 2021/0077015 A1 | 3/2021 | Barrett et al. |
| 2022/0040390 A1 | 2/2022 | Robertson et al. |
| 2022/0387684 A1 | 12/2022 | Borillo et al. |

* cited by examiner

HEMODIALYSIS SYSTEM WITH VARIABLE DIALYSATE FLOW RATE

CROSS-REFERENCE TO RELATED APPLICATIONS

The present application is a continuation of U.S. patent application Ser. No. 17/334,393, filed May 28, 2021, which is hereby incorporated by reference in its entirety.

BACKGROUND OF THE INVENTION

The present invention relates to an artificial kidney system for use in providing dialysis. More particularly, the present invention is directed to a hemodialysis system directed to a hemodialysis system.

Applicant hereby incorporates herein by reference any and all patents and published patent applications cited or referred to in this application.

Hemodialysis is a medical procedure that is used to achieve the extracorporeal removal of waste products including creatine, urea, and free water from a patient's blood involving the diffusion of solutes across a semipermeable membrane. Failure to properly remove these waste products can result in renal failure.

During hemodialysis, the patient's blood is removed by an arterial line, treated by a dialysis machine, and returned to the body by a venous line. The dialysis machine includes a dialyzer containing a large number of hollow fibers forming a semipermeable membrane through which the blood is transported. In addition, the dialysis machine utilizes a dialysate liquid, containing the proper amounts of electrolytes and other essential constituents (such as glucose), that is also pumped through the dialyzer.

Typically, dialysate is prepared by mixing water with appropriate proportions of an acid concentrate and a bicarbonate concentrate. Preferably, the acid and the bicarbonate concentrate are separated until the final mixing right before use in the dialyzer as the calcium and magnesium in the acid concentrate will precipitate out when in contact with the high bicarbonate level in the bicarbonate concentrate. The dialysate may also include appropriate levels of sodium, potassium, chloride, and glucose.

The dialysis process across the membrane is achieved by a combination of diffusion and convection. The diffusion entails the migration of molecules by random motion from regions of high concentration to regions of low concentration. Meanwhile, convection entails the movement of solute typically in response to a difference in hydrostatic pressure. The fibers forming the semipermeable membrane separate the blood plasma from the dialysate and provide a large surface area for diffusion to take place which allows waste, including urea, potassium and phosphate, to permeate into the dialysate while preventing the transfer of larger molecules such as blood cells, polypeptides, and certain proteins into the dialysate.

Typically, the dialysate flows in the opposite direction to blood flow in the extracorporeal circuit. The countercurrent flow maintains the concentration gradient across the semipermeable membrane so as to increase the efficiency of the dialysis. In some instances, hemodialysis may provide for fluid removal, also referred to as ultrafiltration. Ultrafiltration is commonly accomplished by lowering the hydrostatic pressure of the dialysate compartment of a dialyzer, thus allowing water containing dissolved solutes, including electrolytes and other permeable substances, to move across the membrane from the blood plasma to the dialysate. In rarer circumstances, fluid in the dialysate flow path portion of the dialyzer is higher than the blood flow portion, causing fluid to move from the dialysis flow path to the blood flow path. This is commonly referred to as reverse ultrafiltration. Since ultrafiltration and reverse ultrafiltration can increase the risks to a patient, ultrafiltration and reverse ultrafiltration are typically conducted while supervised by highly trained medical personnel.

Unfortunately, hemodialysis suffers from numerous drawbacks. An arteriovenous fistula is the most commonly recognized access point. To create a fistula, a doctor joins an artery and a vein together. Since this process bypasses the patient's capillaries, blood flows rapidly. For each dialysis session, the fistula must be punctured with large needles to deliver blood into, and return blood from, the dialyzer. Typically, this procedure is done three times a week, for 3-4 hours at an out-patient facility. To a lesser extent, patients conduct hemodialysis at home. Home dialysis is typically done for two hours, six days a week. However, home hemodialysis requires more frequent treatment.

Home hemodialysis suffers from still additional disadvantages. Current home dialysis systems are big, complicated, intimidating, and difficult to operate. The equipment requires significant training. Home hemodialysis systems are currently too large to be portable, thereby preventing hemodialysis patients from traveling. Home hemodialysis systems are expensive and require a high initial monetary investment, particularly compared to in-center hemodialysis where patients are not required to pay for the machinery. Present home hemodialysis systems do not adequately provide for the reuse of supplies, making home hemodialysis economically less feasible to medical suppliers. As a result of the above-mentioned disadvantages, very few motivated patients undertake the drudgery of home hemodialysis.

Furthermore, hemodialysis systems utilizing sorbent filters have not been widely accepted. Unfortunately, the sorbent filters are relatively expensive and can be spent quickly due to ion exchange that occurs as excess dialysed ions—K+, Ca++, Mg++ and phosphate ($PO_4$) are exchanged for benign or less toxic ions like Na+, H+, bicarbonate ($HCO3-$) and acetate.

Accordingly, there is a significant need for a hemodialysis system that is transportable, lightweight, easy to use, patient-friendly and thus capable of in-clinic or in-home use.

Moreover, it would be desirable to provide a hemodialysis system that possessed no single-point of failure in the pumps, motors, tubes, or electronics which would endanger a patient.

In addition, it would be desirable to provide a hemodialysis system that was capable of being used in a variety of modes, such as with a filter to cleanse dialysate or without a filter.

In addition, it would be desirable to operate the hemodialysis system in a manner that maximized the life of the sorbent filter.

Aspects of the present invention fulfill these needs and provide further related advantages as described in the following summary.

SUMMARY OF THE INVENTION

According to a first aspect of the invention, a hemodialysis system is provided including an arterial blood line for connecting to a patient's artery for collecting blood from a patient, a venous blood line for connecting to a patient's vein for returning blood to a patient, a reusable dialysis machine and a disposable dialyzer.

The arterial blood line and venous blood line may be typical constructions known to those skilled in the art. For example, the arterial blood line may be traditional flexible hollow tubing connected to a needle for collecting blood from a patient's artery. Similarly, the venous blood line may be a traditional flexible tube and needle for returning blood to a patient's vein. Various constructions and surgical procedures may be employed to gain access to a patient's blood including an intravenous catheter, an arteriovenous fistula, or a synthetic graft.

Preferably, the disposable dialyzer has a construction and design known to those skilled in the art including a blood flow path and a dialysate flow path. The term "flow path" is intended to refer to one or more fluid conduits, also referred to as passageways, for transporting fluids. The conduits may be constructed in any manner as can be determined by those skilled in the art, such as including flexible medical tubing or non-flexible hollow metal or plastic housings. The blood flow path transports blood in a closed loop system by connecting to the arterial blood line and venous blood line for transporting blood from a patient to the dialyzer and back to the patient. Meanwhile, the dialysate flow path transports dialysate in a closed loop system from a supply of dialysate to the dialyzer and back to the dialysate supply. Both the blood flow path and the dialysate flow path pass through the dialyzer, but the flow paths are separated by the dialyzer's semipermeable membrane.

Preferably, the hemodialysis system contains a reservoir for storing a dialysate solution. The reservoir connects to the hemodialysis system's dialysate flow path to form a closed loop system for transporting dialysate from the reservoir to the hemodialysis system's dialyzer and back to the reservoir. Alternatively, the hemodialysis system possesses two (or more) dialysate reservoirs which can be alternatively placed within the dialysate flow path. When one reservoir possesses contaminated dialysate, dialysis treatment can continue using the other reservoir while the reservoir with contaminated dialysate is emptied and refilled. The reservoirs may be of any size as required by clinicians to perform an appropriate hemodialysis treatment. However, it is preferred that the two reservoirs be the same size and sufficiently small so as to enable the dialysis machine to be easily portable. Acceptable reservoirs are 0.5 liters to 6.0 liters in size. Where the hemodialysis system includes only one reservoir, an acceptable reservoir has a volume of 12.0 liters.

The hemodialysis system preferably possesses one or more heaters thermally coupled to the reservoirs for heating dialysate stored within the reservoir. In addition, the hemodialysis system includes temperature sensors for measuring the temperature of the dialysate within the reservoirs. The hemodialysis system preferably possesses a fluid level sensor for detecting the level of fluid in the reservoir. The fluid level sensor may be any type of sensor for determining the amount of fluid within the reservoir. Acceptable level sensors include magnetic or mechanical float type sensors, conductive sensors, ultrasonic sensors, optical interfaces, and weight measuring sensors such as a scale or load cell for measuring the weight of the dialysate in the reservoir.

Preferably, the dialysis includes three primary pumps. The first and second "dialysate" pumps are connected to the dialysate flow path for pumping dialysate through the dialysate flow path from a reservoir to the dialyzer and back to the reservoir. Preferably, a first pump is positioned in the dialysate flow path "upflow", (meaning prior in the flow path) from the dialyzer while the second pumps is positioned in dialysate flow path "downflow" (meaning subsequent in the flow path) from the dialyzer. Meanwhile, the hemodialysis system's third primary pump is connected to the blood flow path. This "blood" pump pumps blood from a patient through the arterial blood line, through the dialyzer, and through the venous blood line for return to a patient. It is preferred that the third pump be positioned in the blood flow path, upflow from the dialyzer.

The hemodialysis system may also contain one or more sorbent filters for removing toxins which have permeated from the blood plasma through the semipermeable membrane into the dialysate. Filter materials for use within the filter are well known to those skilled in the art. For example, suitable materials include resin beds including zirconium based resins. Acceptable materials are also described in U.S. Pat. No. 8,647,506 and U.S. Patent Publication No. 2014/0001112.

In a first embodiment, the sorbent filter is connected to the dialysate flow path downflow from the dialyzer so as to remove toxins in the dialysate prior to the dialysate being transported back to a reservoir. In a second embodiment, the filter is outside of the closed loop dialysate flow path, but instead is positioned within a separate closed loop "filter" flow path that selectively connects to either one of the two dialysate reservoirs. For this embodiment, preferably the hemodialysis system includes an additional fluid pump for pumping contaminated dialysate through the filter flow path and its filter.

Preferably, the hemodialysis system includes two additional flow paths in the form of a "drain" flow path and a "fresh dialysate" flow path. The drain flow path includes one or more fluid drain lines for draining the reservoirs of contaminated dialysate, and the fresh dialysate flow path includes one or more fluid fill lines for transporting fresh dialysate from a supply of fresh dialysate to the reservoirs. One or more fluid pumps may be connected to the drain flow path and/or a fresh dialysate flow path to transport the fluids to their intended destination.

In addition, the hemodialysis system includes a plurality of fluid valve assemblies for controlling the flow of blood through the blood flow path, for controlling the flow of dialysate through the dialysate flow path, and for controlling the flow of used dialysate through the filter flow path. The valve assemblies may be of any type of electro-mechanical fluid valve construction as can be determined by one skilled in the art including, but not limited to, traditional electro-mechanical two-way fluid valves and three-way fluid valves. A two-way valve is any type of valve with two ports, including an inlet port and an outlet port, wherein the valve simply permits or obstructs the flow of fluid through a fluid pathway. Conversely, a three-way valve possesses three ports and functions to shut off fluid flow in one fluid pathway while opening fluid flow in another pathway. In addition, the dialysis machine's valve assemblies may include safety pinch valves, such as a pinch valve connected to the venous blood line for selectively permitting or obstructing the flow of blood through the venous blood line. The pinch valve is provided so as to pinch the venous blood line and thereby prevent the flow of blood back to the patient in the event that an unsafe condition has been detected.

Preferably, the hemodialysis system contains sensors for monitoring hemodialysis. To this end, preferably the dialysis machine has at least one flow sensor connected to the dialysate flow path for detecting fluid flow (volumetric and/or velocity) within the dialysate flow path. In addition, it is preferred that the dialysis machine contain one or more pressure sensors for detecting the pressure within the dialysate flow path, or at least an occlusion sensor for detecting whether the dialysate flow path is blocked. Preferably, the dialysis machine also possesses one or more sensors for measuring the pressure and/or fluid flow within the blood flow path. The pressure and flow rate sensors may be separate components, or pressure and flow rate measurements may be made by a single sensor.

Furthermore, it is preferred that the hemodialysis system include a blood leak detector ("BLD") which monitors the flow of dialysate through the dialysate flow path and detects whether blood has inappropriately diffused through the dialyzer's semipermeable membrane into the dialysate flow path. In a preferred embodiment, the hemodialysis system includes a blood leak sensor assembly incorporating a light source which emits light through the dialysate flow path and a light sensor which receives the light that has been emitted through the dialysate flow path. After passing through the dialysate flow path, the received light is then analyzed to determine if the light has been altered to reflect possible blood in the dialysate.

The dialysis machine preferably includes additional sensors including an ammonia sensor and a pH sensor for detecting the level of ammonia and pH within the dialysate. Preferably, the ammonia sensor and pH sensor are in the dialysate flow path immediately downstream of the filter. In addition, the dialysis machine possesses a bubble sensor connected to the arterial blood line and a bubble sensor connected to the venous blood line for detecting whether gaseous bubbles have formed in the blood flow path.

The hemodialysis system possesses a processor containing the dedicated electronics for controlling the hemodialysis system. The processor contains power management and control electrical circuitry connected to the pump motors, valves, and dialysis machine sensors for controlling proper operation of the hemodialysis system.

It has been found that decreasing the flow rate of the dialysate through the dialysate flow path increases the capacity of the sorbent filter's zirconium phosphate to capture ammonium from urea. Because urea is high at the beginning of a patient's treatment and then decreases as it is removed during treatment, a constant urea concentration requires starting at a high flowrate and reducing it over the course of the treatment. Advantageously any losses of urea clearance from decreasing the dialysate flow rate can be compensated for by extending the duration of the dialysis treatment. Accordingly, in a preferred embodiment, the hemodialysis system's processor includes memory which stores one or more patient treatment plans by which a patient is treated. In accordance with the patient treatment plan, the dialysate flow rate through the dialysate flow path is not static throughout treatment. Instead, the dialysate flow rate decreases throughout the patient's treatment. The decrease in dialysate flow rate may be incremental. Alternatively, the dialysate flow rate may be decrease in any manner such as linear, exponential, inverse, polynomial, or other relationship which provides for decreasing the dialysate flow rate over time.

Specifically, each patient treatment plan includes a total time period "T(total)" for treating a patient which in turn comprises a plurality of time segments including time segment T1, time segment T2, time segment T3, etc. The patient treatment plan further including a plurality of flow rates including at least a high flow rate which operates for time segment T1, time segment T2, time segment T3, etc. As would be understood by those skilled in the art, where the decrease in dialysate flow rate is changed slowly, such as in a linear or polynomial manner, the time period for each time segment may be extremely small.

Preferably, the dialysate treatment starts at a higher dialysate flow rate between 400 to 800 ml/min and the ends at a lower flow rate between 100 to 500 ml/min. More preferably, the dialysate treatment starts at a higher dialysate flow rate between 450 to 800 ml/min and the ends at a lower flow rate between 100 to 450 ml/min. In a preferred embodiment, the patient treatment plan lasts two-six hours and begins treatment with a dialysate flow rate of approximately 400 to 600 ml/min and decreases linearly until ending at a flow rate between 200 to 300 ml/min. In still a more preferred embodiment, the patient treatment plan begins treatment with a dialysate flow rate of approximately 500 ml/min and decreases linearly for four hours until ending at a flow rate of 250 ml/min.

The dialysis machine provides a hemodialysis system that is transportable, lightweight, easy to use, patient-friendly and capable of in-home use.

In addition, the hemodialysis system provides an extraordinary amount of control and monitoring not previously provided by hemodialysis systems so as to provide enhanced patient safety.

Moreover, the hemodialysis system maximizes the amount of urea that can be removed by the sorbent filter.

Other features and advantages of the present invention will be appreciated by those skilled in the art upon reading the detailed description, which follows with reference to the Drawings.

DETAILED DESCRIPTION OF THE INVENTION

Figure 1:
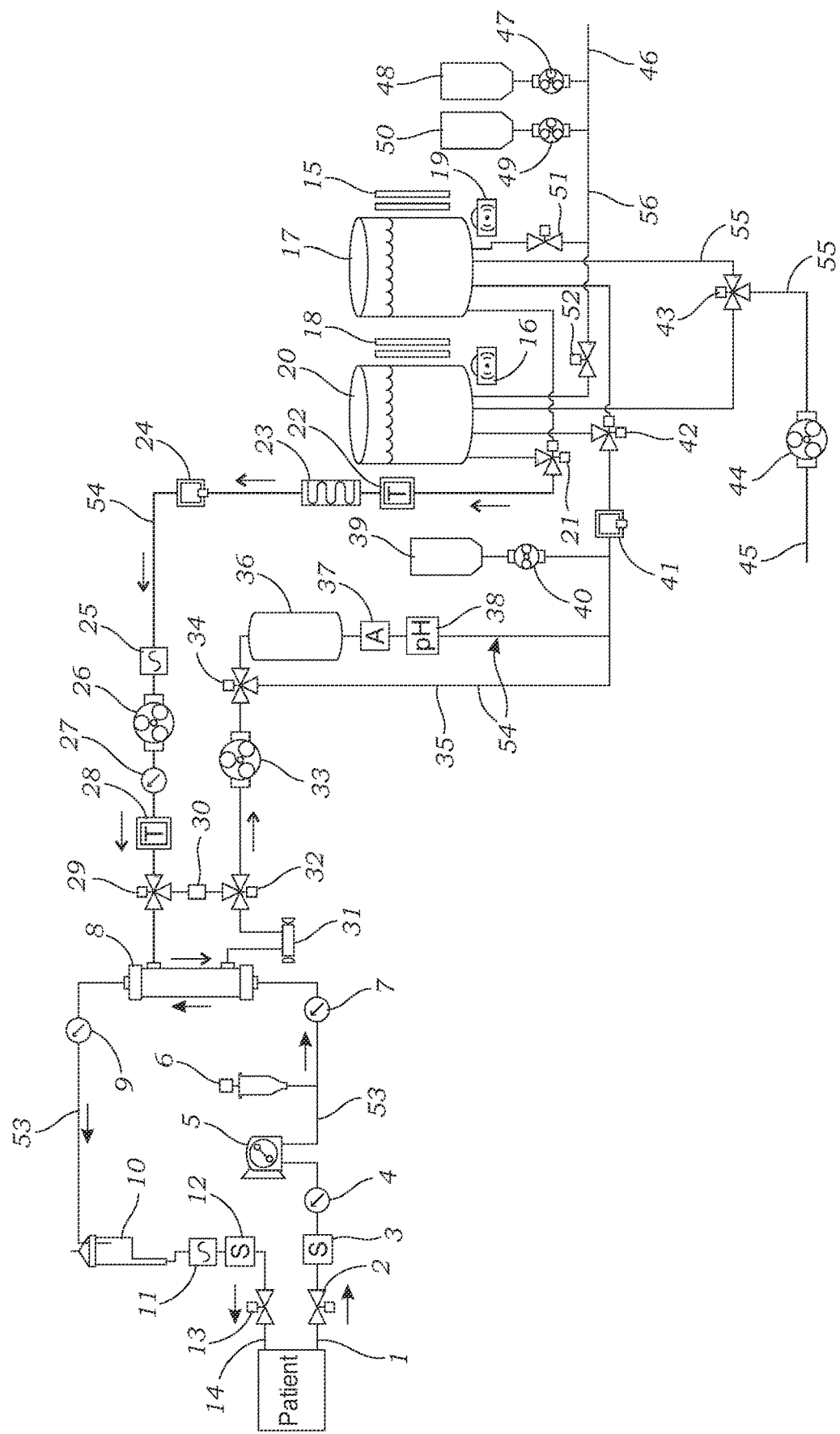
FIG. 1 is a flow chart illustrating a first embodiment of the hemodialysis system.

While the present invention is capable of embodiment in various forms, as shown in the drawings, hereinafter will be described the presently preferred embodiments of the invention with the understanding that the present disclosure is to be considered as an exemplification of the invention, and it is not intended to limit the invention to the specific embodiments illustrated.

As best illustrated in FIGS. 1-8, the hemodialysis system includes a blood flow path 53 and a dialysate flow path 54. The hemodialysis system further includes a reusable dialysis machine and disposable components for performing hemodialysis. The blood flow path 53 includes an arterial blood line 1 for connecting to a patient's artery for collecting blood from a patient, and a venous blood line 14 for connecting to a patient's vein for returning blood to a patient. The arterial blood line 1 and venous blood line 14 may be typical constructions known to those skilled in the art.

The blood flow path 53 transports blood in a closed loop system by connecting to the arterial blood line 1 and venous blood line 14 to a patient for transporting blood from a patient through the dialyzer 8 and back to the patient. Preferably, the hemodialysis system includes a supply of heparin 6 and a heparin pump connected to the blood flow path 1. The heparin pump delivers small volumes of heparin anticoagulant into the blood flow to reduce the risk of blood clotting in the machine. The heparin pump can take the form of a linearly actuated syringe pump, or the heparin pump may be a bag connected with a small peristaltic or infusion pump.

The hemodialysis system includes a dialyzer 8 in the dialysate flow path 54 which is of a construction and design known to those skilled in the art. Preferably, the dialyzer 8 includes a large number of hollow fibers which form a semipermeable membrane. Suitable dialyzers can be obtained from Fresenius Medical Care, Baxter International, Inc., Nipro Medical Corporation, and other manufacturers of hollow fiber dialyzers. Both the blood flow path and dialysate flow path travel through the dialyzer 8 which possesses an inlet for receiving dialysate, an outlet for expelling dialysate, an inlet for receiving blood from a patient, and an outlet for returning blood to a patient. Preferably, the dialysate flows in the opposite direction to the blood flowing through the dialyzer with the dialysate flow path isolated from the blood flow path by a semipermeable membrane (not shown). As illustrated in FIGS. 1-6 and as explained in greater detail below, the dialysate flow path 54 transports dialysate in a closed loop system in which dialysate is pumped from a reservoir (17 or 20) to the dialyzer 8 and back to the reservoir (17 or 20). Both the blood flow path 53 and the dialysate flow path 54 pass through the dialyzer 8, but are separated by the dialyzer's semipermeable membrane.

Preferably, the hemodialysis system includes three primary pumps (5, 26 & 33) for pumping blood and dialysate. For purposes herein, the term "pump" is meant to refer to both the pump actuator which uses suction or pressure to move a fluid, and the pump motor for mechanically moving the actuator. Suitable pump actuators may include an impeller, piston, diaphragm, the lobes of a lobe pump, screws of a screw pump, rollers or linear moving fingers of a peristaltic pump, or any other mechanical construction for moving fluid as can be determined by those skilled in the art. Meanwhile, the pump's motor is the electromechanical apparatus for moving the actuator. The motor may be connected to the pump actuator by shafts or the like. In a preferred embodiment, the dialysate and/or blood flow through traditional flexible tubing and each of the pump actuators consist of a peristaltic pump mechanism wherein each pump actuator includes a rotor with a number of cams attached to the external circumference of the rotor in the form of "rollers", "shoes", "wipers", or "lobes" which compress the flexible tube. As the rotor turns, the part of the tube under compression is pinched closed (or "occludes") forcing the fluid to be pumped through the tube. Additionally, as the tube opens to its natural state after the passing of the cam fluid flow is induced through the tube.

The first and second primary pumps (26 & 33) are connected to the dialysate flow path for pumping dialysate through the dialysate flow path from a reservoir (17 or 20) to the dialyzer 8 and back to the reservoir (17 or 20). A first pump 26 is connected to the dialysate flow path "upstream", (meaning prior in the flow path) from the dialyzer 8 while the second pump 33 is connected to the dialysate flow path "downstream" (meaning subsequent in the flow path) from the dialyzer 8. Meanwhile, the hemodialysis system's third primary pump 6 is connected to the blood flow path. The third pump 6, also referred to as the blood pump, pumps blood from a patient through the arterial blood line, through the dialyzer 8, and through the venous blood line for return to a patient. It is preferred that the third pump 6 be connected to the blood flow path upstream from the dialyzer. The hemodialysis system may contain more or less than three primary pumps. For example, the dialysate may be pumped through the dialyzer 8 utilizing only a single pump. However, it is preferred that the hemodialysis system contain two pumps including a first pump 26 upstream from the dialyzer 8 and a second pump 33 downflow from the dialyzer 8.

Preferably, the hemodialysis system contains one or more reservoirs (17 & 20) for storing dialysate solution. Where the system includes two reservoirs, both of the reservoirs (17 and 20) may be connected simultaneously to the dialysate flow path 54 to form one large source of dialysate. Alternatively, the hemodialysis system includes a valve assembly 21 for introducing either, but not both, of the two reservoirs (17 or 20) into the dialysate flow path 54 to form a closed loop system for transporting a dialysate from one of the two reservoirs to the dialyzer and back to that reservoir. After the dialysate in a first reservoir 17 has been used, is no longer sufficiently clean, or does not possess appropriate chemical properties, the hemodialysis system's valve 21 is controlled to remove the first reservoir 17 from the dialysate flow path and substitute the second reservoir 20, which has fresh dialysate 75, into the dialysate flow path. Thus, when one reservoir possesses contaminated dialysate 76, and the reservoir needs to be emptied and refilled with freshly generated dialysis fluid 75, dialysis treatment can continue using the other reservoir.

In this manner, the hemodialysis system may switch between each reservoir 17 and 20 times over the course of the treatment. Furthermore, the presence of two reservoirs as opposed to one reservoir allows for the measurement of the flow rate for pump calibration or ultrafiltration measurement, while isolating the other reservoir while it is being drained or filled. Though the reservoirs may be of any size as required by clinicians to perform an appropriate hemodialysis treatment, preferred reservoirs have a volume between 0.5 liters and 5.0 liters.

The hemodialysis system also contains a sorbent filter (also referred to herein as a "filter") connected to the dialysate flow path 54 for removing toxins which have permeated from the blood plasma through the semipermeable membrane into the dialysate. In a first embodiment, the filter 36 is connected to the dialysate flow path 54 downstream from the dialyzer so as to remove toxins transferred by the dialyzer into the dialysate prior to the dialysate being transported to the reservoir. Filter materials for use with the dialysis machine are well known to those skilled in the art. For example, suitable materials include resin beds including zirconium based resins. Preferably, the filter has a housing containing layers of zirconium oxide, zirconium phosphate and carbon. Acceptable materials are described in U.S. Pat. No. 8,647,506 and U.S. Patent Application Publication No. 2014/0001112. Other acceptable filter materials can be developed and utilized by those skilled in the art without undue experimentation. The filter housing may or may not include a vapor membrane capable of releasing gases, but not liquids, and particularly not the dialysate liquid flowing through the filter.

In the event that the hemodialysis system possesses a sorbent filter, preferably the dialysis flow path 54 incorporates safety features in the form of an ammonium sensor 37 and a pH sensor 38. These sensors may be located immediately downstream of the sorbent cartridge 36, or immediately downstream of the one or more reservoirs. When the sorbent filter (36) has been exhausted, the filter 36 may begin to release ammonium ions as a result of the filtering chemical reaction. At certain levels, ammonium ions in the dialysis fluid can harm the patient. Preferably, the ammonium ion sensor 37 measures the quantity of ammonium ions in parts per million (ppm). When the measurement reaches a range of approximately 5 to 20 ppm, a warning state will be activated, and treatment with this dialysate is stopped. The dialysis fluid can be drained, and dialysis treatment may continue by using fresh dialysis fluid using the alternative reservoir. Similarly, the pH sensor 38 also acts as a safety feature and supports the measurement of ammonium ions. As the pH of the dialysis fluid changes, the equilibrium state of ammonia (NH3) and ammonium ions (NH4+) can change. If the pH of the dialysis fluid is measured to be outside the range of approximately 6.4 to 7.8 pH, a warning state can be activated, and the dialysis fluid in use can be drained.

It is also preferred that the hemodialysis system possesses a reagent bag 39 and pump 40 for introducing reagents into the dialysate flow path 54 immediately after the sorbent filter 36. The reagent bag (39) holds a concentrated solution of salts and ions to reinfuse the filter dialysis fluid. Through the action of filtering waste, the sorbent filter (36) also removes beneficial ions from the dialysis fluid, such as calcium and salt. Before the filtered dialysis fluid can be recirculated, it must be reinfused with calcium and salts so that the dialysis fluid does not draw these beneficial ions from the patient's blood. Preferably, the reagent bag 39 will hold between 1 and 3 liters of concentrated reagent. The reagent pump 40 can be any type of pump such as a peristaltic pump or diaphragm pump. To ensure that the hemodialysis system is introducing the proper amount of salts and ions into the dialysate, a conductivity sensor 41 may be positioned within the dialysate flow path 54 immediately after the reagent bag 39. The conductivity sensor 41 serves as a safety feature, measuring the total dissolved solids of the regenerated dialysis fluid. In the event that the total dissolved solids are detected to not be within a prescribed range, the operation of the pump 40 can be increased or decreased, or alternatively, treatment can be stopped entirely. For example, if a fault state is detected in the dialysis fluid, then the fluid can be redirected by 3-way valves 29 and 32 through the bypass path 30 so that dialysate does not meet the patient's blood in the dialyzer. More specifically, the 3-way valve 29 directs dialysis fluid to the dialyzer's inlet and the 3-way valve 32 directs dialysate from the dialysate outlet back through the dialysate flow path 54. However, if a fault state is detected in the dialysis fluid, such as the temperature being too low or excessive ammonium ions are detected in the dialysate, then the dialysis fluid is redirected by 3-way valves 29 and 32 to bypass the dialyzer 8, through bypass path 30.

For the embodiment illustrated in FIGS. 1-4, the hemodialysis system includes a drain flow path 55 to dispose of waste dialysate from the reservoirs (17 and 20). In the embodiment illustrated in the FIGS. 1-4, the drain flow path 55 is connected to both reservoirs (17 and 20). Waste dialysate may drain through the drain flow path 5 through a gravity feed, or the hemodialysis system may include a pump 44 of any type as can be selected by those skilled in the art to pump used dialysate to be discarded, such as to a traditional building sewer line 45.

For the embodiment illustrated in FIGS. 1-4, the hemodialysis system preferably includes a source 46 of dialysate fluid to replenish each of the reservoirs 17 and 20. Preferably, the source of dialysate fluid includes a supply of clean water 46 that is mixed with reagents (48 & 50) to provide dialysate of desired properties. In a preferred embodiment, the supply of clean water 46 is provided by a reverse osmosis ("RO") machine located adjacent to the device which produces clean water and then adds chemical concentrates to create the dialysate fluid. The fluid is supplied through a "fresh dialysate" flow path 56 to the reservoirs (17 & 20). Preferably, the hemodialysis system also includes a source of concentrated reagents (48 & 50) which may be stored in disposable bags. Preferably, the concentrated reagents contain one or more of the following: carbonate solution, bicarbonate solution, acid solution, lactate solution, salt solution. It is necessary to separate some of the reagents into two bags (48 & 50) to prevent undesirable interactions or precipitation of solutes. The source of concentrated reagents (48 and 50) are connected by pumps (47 & 49) to the supply line 46. The activation of the pumps (47 and 49) introduces the concentrated reagents into the supply of water to provide dialysate to the reservoirs (17 and 20).

As an alternative to using the sorbent filter 36, the hemodialysis system includes a supplemental "bypass" flow path 35 that selectively transports dialysis around the sorbent filter 36. The bypass flow path includes a 3-way valve 34 upstream of the filter. The 3-way valve 34 is switched to direct the dialysis fluid through sorbent filter 36, or alternatively, the 3-way valve 34 is switched to direct dialysate through the bypass flow path 35 to avoid the sorbent filter 36. For example, if a sorbent filter is not available, or if the sorbent filter has become spent, or if a sorbent filter is not required for a particular patient treatment, then the 3-way valve 34 is switched to direct the dialysis fluid down the bypass flow path 35.

Figure 5:
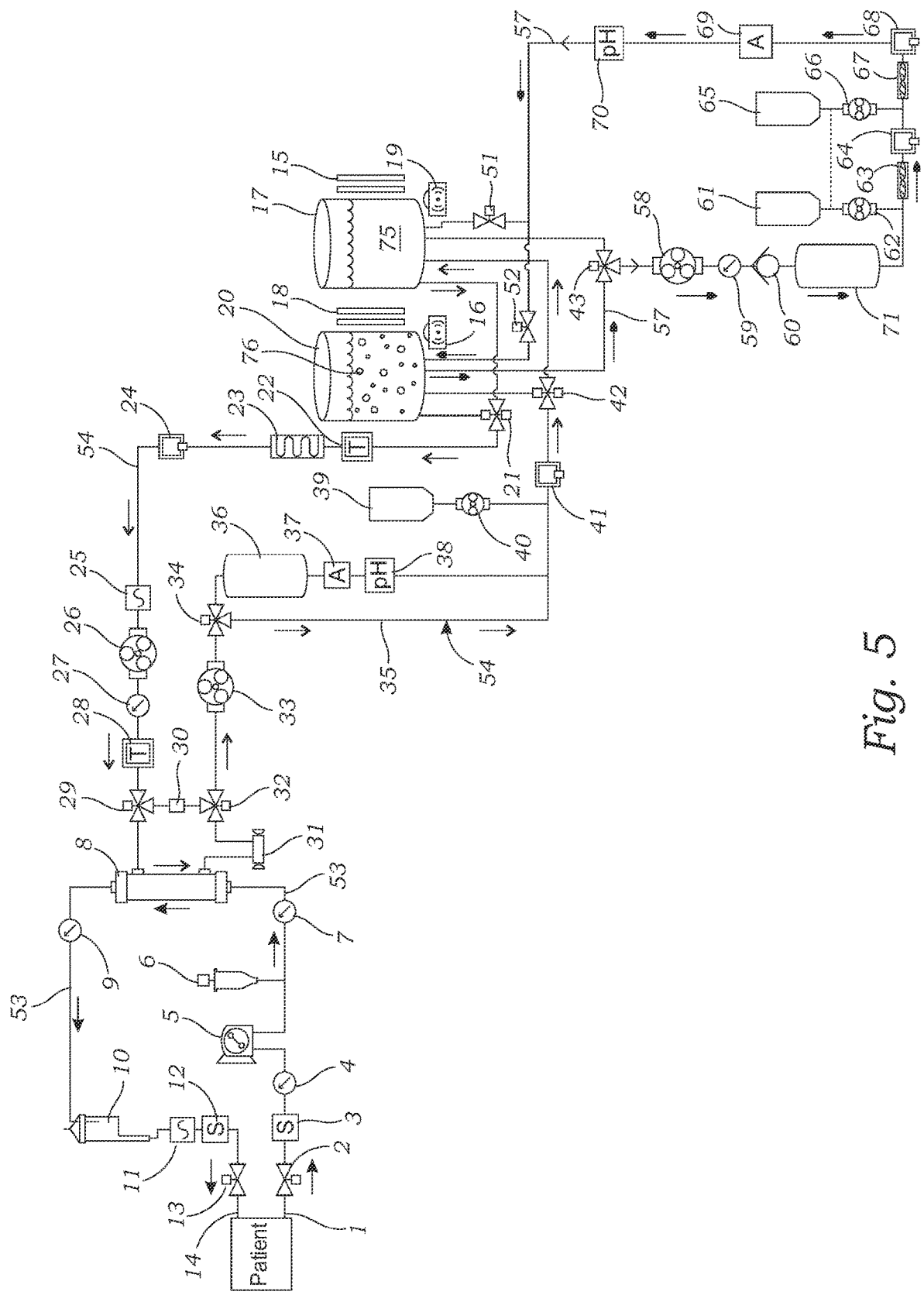
FIG. 5 is a flow chart illustrating a second embodiment of the hemodialysis system including a closed loop filter flow path which is filtering the fluid in a first reservoir.
Figure 6:
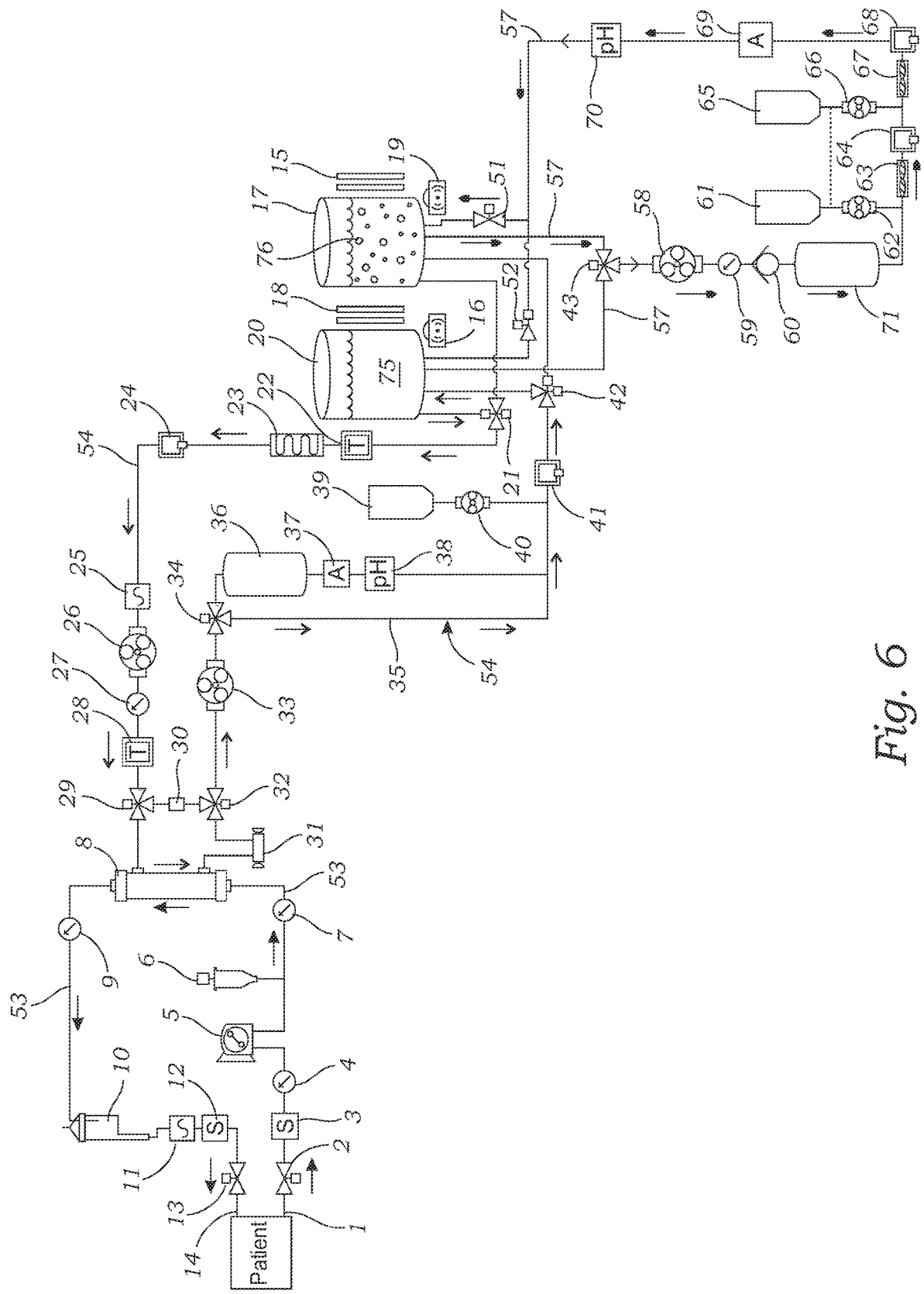
FIG. 6 is a flow chart illustrating the second embodiment of the hemodialysis system shown in FIG. 5 wherein the filter flow path which is filtering the fluid in a second reservoir.

In an alternative embodiment illustrated in FIGS. 5 and 6, the sorbent filter 71 is located outside of the closed loop dialysate flow path. The hemodialysis system includes a separate closed loop "filter" flow path 57 that selectively connects to either one of the two dialysate reservoirs 17 or 20, and the filter 71 is positioned in-series in the closed loop filter flow path 57. Preferably, the dialysis machine includes an additional fluid pump 58 for pumping contaminated dialysate through the filter flow path and the filter 71. As illustrated in FIGS. 5 and 6, a preferred filter flow path 57 includes a 3-way valve 43 which determines which reservoir is drained of contaminated dialysate. For example, FIG. 5 illustrates the 3-way valve 43 connecting reservoir 20, but not reservoir 17, to the filter flow path 57. FIG. 6 illustrates the 3-way valve 43 connecting reservoir 17, but not reservoir 20, to the filter flow path 57. The filter flow path may include a pump 58, or the dialysate may dispense contaminated dialysate from reservoirs 17 or 20 through a gravity feed. In addition, preferably the filter flow path 57 includes a pressure sensor 59, a check valve 60, an ammonium sensor 69, and a pH sensor 70.

This embodiment of the hemodialysis machine includes a system for introducing reagents into the filter flow path. As illustrated in FIGS. 5 and 6, the filter flow path 57 may include a first reagent source 61 containing salts and a second reagent source 65 containing bicarbonate and lactate solution. These reagents are introduced into the filter flow path using pumps 62 and 66, and mixers 63 and 67. Preferably the filter flow path also possesses safety features in the form an ammonium sensor 69 to ensure that the filter 71 is not spent and introducing unacceptable ammonium ions into the dialysate, and conductivity sensors 64 and 68 which monitor whether the reagents have been properly introduced into the cleaned dialysate to provide the proper amounts of beneficial ions. Finally, the filter flow path 57 includes a pair of check valves 51 and 52 which are opened or closed to ensure that the now cleaned dialysate is returned to the reservoir from which the contaminated dialysate had been drained from.

Figure 7:
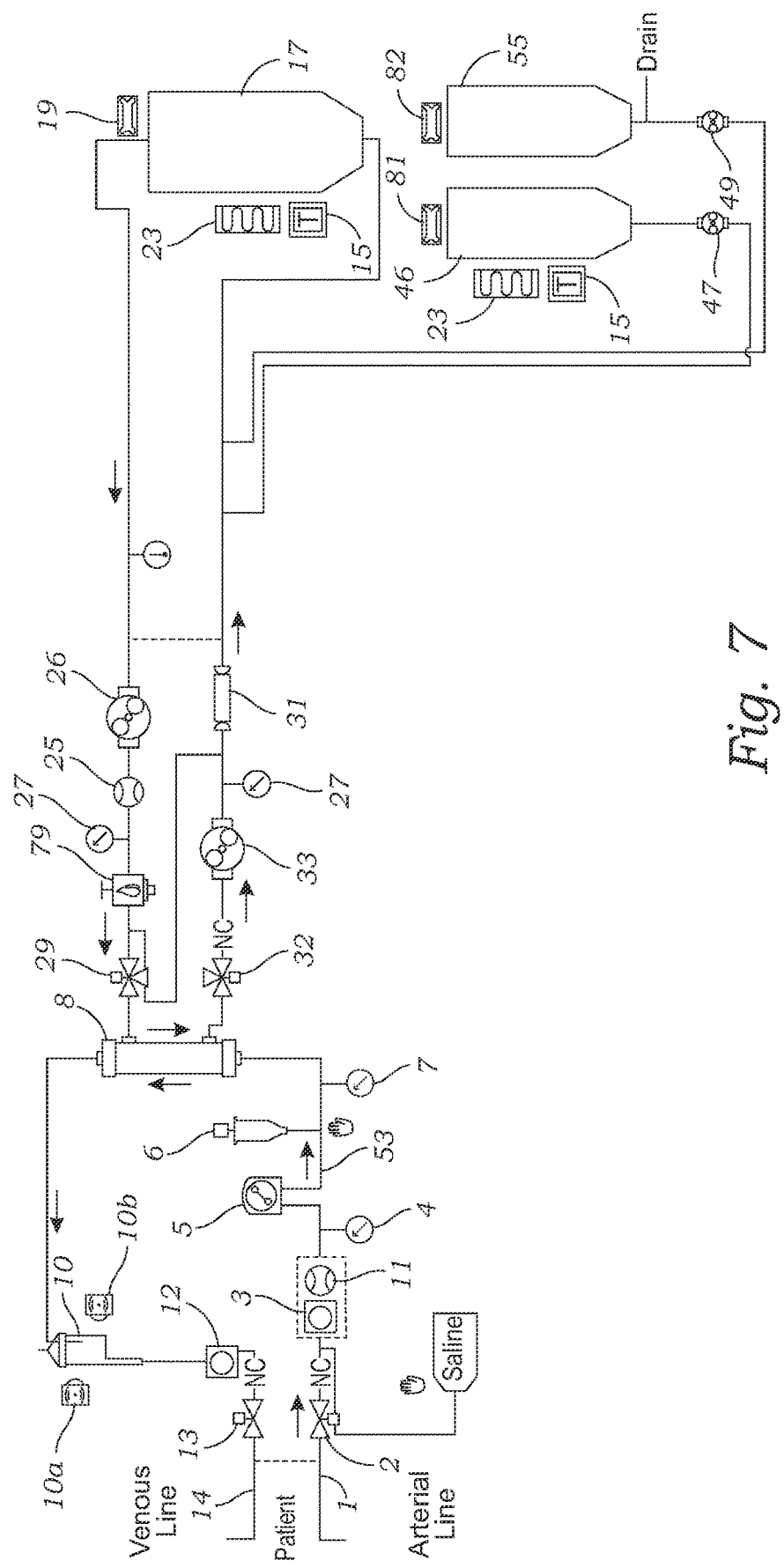
FIG. 7 is the flow chart illustrating an embodiment of the hemodialysis system where dialysate from an outside source is supplied to one of the system's reservoirs, and used dialysate is directed to a storage bag or to a drain.

FIG. 7 illustrates an embodiment of the hemodialysis system where the system is operated in a single pass mode. Dialysate is introduced to the machine through the fresh dialysate flow path to the reservoir 17 from a source of dialysate 46 which is maintained at a desired temperature by a heater 23. For this treatment, the dialysate from the first reservoir 17 is circulated through the dialyzer 8 using pumps 26 and 33. Thereafter, used dialysate is then directed to a receptacle for storing waste water 55, or an effluent drain. Load cells 81 and 82 and/or a level sensors 15 may be provided to measure the source of dialysate 46 and the resulting waste water 55. Furthermore, the dialysate flow path may include a flow sensor 25, pressure sensors 27, and a sample port 79.

Figure 8:
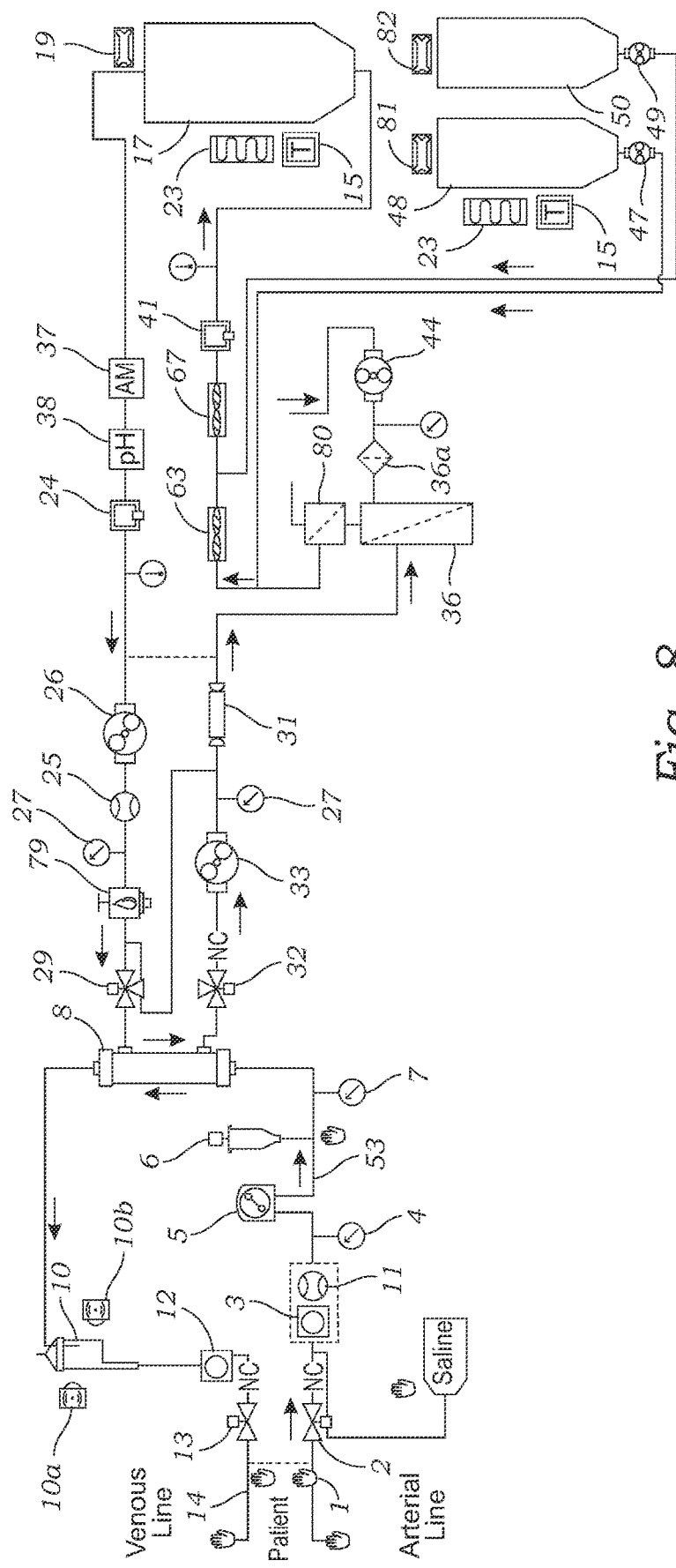
FIG. 8 is the flow chart illustrating the embodiment of the hemodialysis system in FIG. 7 wherein a sorbent filter has been introduced into the system to provide a closed-loop operation.
Figure 9:
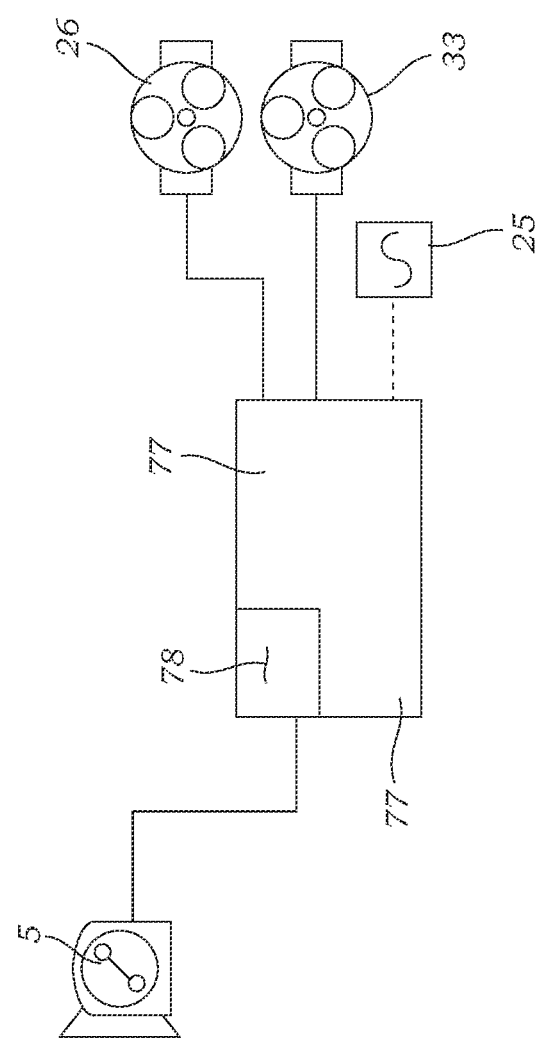
FIG. 9 is a block diagram illustrating the blood pump, dialysate pumps, and flow sensor connected to the hemodialysis system's processor.

FIG. 8 illustrates still an additional embodiment of the hemodialysis system which operates in recirculating mode where the dialysate flows in a closed-loop system through the sorbent filter 36. Like other embodiments, the blood flow path 53 transports blood in a closed loop system by connecting to the arterial blood line 1 and venous blood line 14 to a patient for transporting blood from a patient to the dialyzer and back to the patient. Dialysate is stored in a reservoir 17 with the level of dialysate's measured by a level sensor 15 and load cell 19, and the dialysate's temperature maintained by a heater 23. Dialysate is recirculated through the dialyzer 8 and sorbent cartridge 36 using pumps 26 and 33. Thereafter, the dialysate is sent back to the same reservoir 17 through the dialysate flow path 54.

In the embodiment illustrated in FIG. 8, sources of chemical concentrates 48 and 50 are provided which can be added to the fluid leaving the sorbent filter, as necessary, to maintain proper chemicals in the dialysate. Preferably, the first reagent source 48 contains salts and a second reagent source 50 contains bicarbonate or carbonate and lactate solution. The chemical concentrates are introduced into the dialysate flow path using the chemical concentrate pumps 47 and 49 where the clean water and chemical concentrates are mixed with mixers 63 and 67. Again, the dialysate flow path may include a flow sensor 25, pressure sensors 27, and a sample port 79. Preferably, the dialysate flow path also includes a conductivity sensor 41 positioned between the second mixer 67 and reservoir 17, and includes an ammonia sensor 37, a pH sensor 38 and a combined conductivity/temperature sensor 24 positioned between the reservoir 17 and dialyzer 8. A control processor is connected to the various sensors and pumps to control the hemodialysis treatment. With reference also to FIGS. 9-13, preferably the control processor causes the flow rate of the dialysate to decrease throughout the treatment, as described below.

With reference still to FIGS. 1-8, the hemodialysis system preferably possesses a heater 23 thermally connected to the dialysate flow path or to reservoirs for heating the dialysate to a desired temperature. For example, in an embodiment illustrated in FIGS. 1-6, a single heater 23 is thermally coupled to the dialysate flow path downstream of both reservoirs (17 & 20). However, the hemodialysis may include additional heaters, and the one or more heaters may be in different locations. For example, in an alternative embodiment, the hemodialysis system includes two heaters, with a single heater thermally coupled to each reservoir. The one or more heaters are preferably activated by electricity and includes a resistor which produces heat with the passage of an electric current.

In addition, the hemodialysis system possesses various sensors for monitoring hemodialysis, and in particular, the dialysate flow path and blood flow path. To this end, the hemodialysis system preferably has one or more flow sensors 25 connected to the dialysate flow path for detecting fluid flow (volumetric and/or velocity) within the dialysate flow path. In addition, it is preferred that the hemodialysis system contain one or more pressure, or occlusion, sensors (9 & 27) for detecting the pressure within the dialysate flow path. Preferably, the hemodialysis system also possesses one or more sensors for measuring the pressure (4 & 7) and/or fluid flow 11 within the blood flow path.

Preferably, the hemodialysis system includes temperature sensors (22, 24 and 28) for measuring the temperature of the dialysate throughout the dialysate flow path. In addition, the hemodialysis system possesses level sensors for detecting the level of fluid in the reservoirs (17 and 20). Preferred level sensors may include either capacitive fluid level sensors (15 and 18) embodiment, the weight, and therefore level of dialysate, of each reservoir 17 and 20 is measured by a level sensor (16 or 19) connected to the processor.

Furthermore, it is preferred that the hemodialysis system includes a blood leak detector 31 which monitors the flow of dialysate through the dialysate flow path and detects whether blood has inappropriately diffused through the dialyzer's semipermeable membrane into the dialysate flow path.

Preferably, the hemodialysis system also contains a first pinch valve 2 connected to the arterial blood line 1 for selectively permitting or obstructing the flow of blood through the arterial blood line, and a second pinch valve 13 connected to the venous blood line 14 for selectively permitting or obstructing the flow of blood through the venous blood line. The pinch valves are provided so as to pinch the arterial blood line 1 and venous blood line 14 to prevent the flow of blood back to the patient in the event that any of the sensors have detected an unsafe condition. Providing still additional safety features, the hemodialysis system includes blood line bubble sensors (3 & 12) to detect if an air bubble travels backwards down the arterial line (blood leak sensor 3) or venous line (blood leak sensor 12). Further, the blood flow path 53 may include a bubble trap 10 which has a pocket of pressurized air inside a plastic housing. Bubbles rise to the top of the bubble trap, while blood continues to flow to the lower outlet of the trap. This component reduces the risk of bubbles traveling into the patient's blood.

To control the flow and direction of blood and dialysate through the hemodialysis system, the hemodialysis system includes a variety of fluid valves for controlling the flow of fluid through the various flow paths of the hemodialysis system. The various valves include pinch valves and 2-way valves which must be opened or closed, and 3-way valves which divert dialysate through a desired flow pathway as intended. In addition to the valves identified above, the hemodialysis system includes a 3-way valve 21 located at the reservoirs' outlets which determines from which reservoir (17 or 20) dialysate passes through the dialyzer 8. An additional 3-way valve 42 determines to which reservoir the used dialysate is sent to. Finally, 2-way valves 51 and 52 (which may be pinch valves) are located at the reservoirs' inlets to permit or obstruct the supply of fresh dialysate to the reservoirs 17 & 20). Of course, alternative valves may be employed as can be determined by those skilled in the art, and the present invention is not intended to be limited the specific 2-way valve or 3-way valve that has been identified.

In addition, the hemodialysis system includes a processor 77 and a user interface (not shown). The processors contains the dedicated electronics for controlling the hemodialysis system including the hardware and software, and power management circuitry connected to the pump motors, sensors, valves and heater for controlling proper operation of the hemodialysis system. The processor monitors each of the various sensors to ensure that hemodialysis treatment is proceeding in accordance with a preprogrammed procedure input by medical personnel into the user interface. The processor may be a general-purpose computer or microprocessor including hardware and software as can be determined by those skilled in the art to monitor the various sensors and provide automated or directed control of the heater, pumps, and pinch valve. The processor may be located within the electronics of a circuit board or within the aggregate processing of multiple circuit boards and memory cards.

Also not shown, the hemodialysis system includes a power supply for providing power to the processor, user interface, pump motors, valves and sensors. The processor is connected to the dialysis machine sensors (including reservoir level sensors (15, 16, 18 and 19), blood leak sensor 31, ammonia sensor 37, pressure and flow rate sensors (4, 7, 9, 11, 25 & 27), temperature sensors (22, 24 & 28), blood line bubble sensors (3 & 12), pumps (5, 6, 26, 33, 40, 44, 47 & 49), and pinch valves (2 & 13) by traditional electrical circuitry.

In operation, the processor is electrically connected to the first, second and third primary pumps (5, 26, & 33) for controlling the activation and rotational velocity of the pump motors, which in turn controls the pump actuators, which in turn controls the pressure and fluid velocity of blood through the blood flow path and the pressure and fluid velocity of dialysate through the dialysate flow path. By independently controlling operation of the dialysate pumps 26 and 33, the processor can maintain, increase or decrease the pressure and/or fluid flow within the dialysate flow path within the dialyzer. Moreover, by controlling all three pumps independently, the processor can control the pressure differential across the dialyzer's semipermeable membrane to maintain a predetermined pressure differential (zero, positive or negative), or maintain a predetermined pressure range. For example, most hemodialysis is performed with a zero or near zero pressure differential across the semipermeable membrane, and to this end, the processor can monitor and control the pumps to maintain this desired zero or near zero pressure differential. Alternatively, the processor may monitor the pressure sensors and control the pump motors, and in turn pump actuators, to increase and maintain positive pressure in the blood flow path within the dialyzer relative to the pressure of the dialysate flow path within the dialyzer. Advantageously, this pressure differential can be affected by the processor to provide ultrafiltration and the transfer of free water and dissolved solutes from the blood to the dialysate.

In the preferred embodiment, the processor monitors the blood flow sensor 11 to control the blood pump flowrate. It uses the dialysate flow sensor 25 to control the dialysate flow rate from the upstream dialysate pump. The processor then uses the reservoir level sensors (15, 16, 18 & 19) to control the flowrate from the downstream dialysate pump 33. The change in fluid level (or volume) in the dialysate reservoir is identical to the change in volume of the patient. By monitoring and controlling the level in the reservoir, forward, reverse, or zero ultrafiltration can be accomplished.

With reference to FIGS. 3, 4, and 8-13, where the hemodialysis system is operating with the dialysate flowing in a closed loop through the sorbent filter 36, preferably the dialysate flow rate is reduced throughout a patient's treatment. More specifically, it has been discovered that greater urea can be removed during treatment using the same sorbent cartridge 36 if the duration of treatment is increased. This is illustrated in the table below which indicates, for example, the same spKt/V can be achieved with a dialysate flow rate at 600 ml/min for 240 minutes as a treatment with a dialysate flow rate at 300 ml/min for 285 minutes. However, the sorbent cartridge 36 is capable or absorbing more urea during treatment operated at the lower dialysate flow rate in accordance with the latter treatment protocol wherein the % change in spKt/V is measured from the baseline numbers shown in bold.

| | 35 L Patient Distribution Volume | | | | 35 L Patient Distribution Volume % | | | |
|---|---|---|---|---|---|---|---|---|
| | A | B | C | D | A | B | C | D |
| Dialysate | Treatment Length | | | | | | | |
| Flow Rate (ml/min) | 240 min | 255 min | 270 min | 285 min | 240 min | 255 min | 270 min | 285 min |
| | spKt/V | | | | % Change in spKt/V from baseline | | | |
| 300 | 1.44 | 1.53 | 1.61 | 1.69 | −16.0 | −9.9 | −4.8 | 0.0 |
| 400 | 1.57 | 1.66 | 1.76 | 1.86 | −7.4 | −1.8 | 4.1 | 9.6 |
| 500 | 1.64 | NA | NA | NA | −3.0 | NA | NA | NA |
| 600 | 1.69 | NA | NA | NA | 0.0 | NA | NA | NA |

Also of importance, urea is typically released into the dialysate at greater levels at the beginning of a hemodialysis treatment compared to the end of treatment. Thus, a higher dialysate flow rate at the beginning of treatment is preferred. To balance these counteracting influences, it is preferred that a patient's treatment commence with the dialysate flowing at a high flow rate at the beginning of treatment, but that dialysate flow rate decrease through a patient's treatment.

There are other reasons besides optimizing urea removal in a Sorbent Filter to change the dialysate flowrates over the course of a treatment. Balancing the volume of dialysate needed for a treatment with the length of a treatment can be accomplished by varying the dialysate flowrate over the course of the treatment. When the urea concentration is high at the beginning of treatment, a high dialysate flowrate is helpful in quickly removing urea from the blood. As the urea concentration decreases, decreasing the flowrate does not overly change the urea that can be removed from the blood, but the amount of dialysate consumed can be decreased.

To implement the patient treatment plan with decreasing dialysate flow rate, the processor 77 is connected to the dialysate flow sensor 25 to monitor the flow of dialysate, and the processor 77 is connected to the dialysate pumps 26 and 33 to control the rate that dialysate flows through the dialysate flow path. In addition, the processor 77 includes memory 78 which stores one or more patient treatment plans by which a patient is treated. The patient treatment plan includes the desired flow rates that dialysate is intended to flow at different time segments throughout the patient's treatment. As illustrated in FIGS. 10-13, in accordance with the patient treatment plan, the dialysate flow rate decreases throughout the patient's treatment. The decrease in dialysate flow rate may be incremental, as illustrated in FIG. 11. Alternatively, the dialysate flow rate may decrease in linear manner as illustrated in FIG. 12. In still alternative treatment plans, the decrease in the dialysate flow rate may be exponential, inverse, polynomial, or another relationship which provides for decreasing the dialysate flow rate over time. For example, FIG. 12 illustrates an acceptable polynomial treatment protocol where the rate of change (Δ) of the decreasing flow rate is decreasing. Conversely, FIG. 13 illustrates an acceptable polynomial treatment protocol where the rate of change (Δ) of the decreasing flow rate is increasing.

Specifically, each patient treatment plan includes a total time period "T(total)" for treating a patient which in turn comprises a plurality of time segments including time segment T1, time segment T2, time segment T3, etc. The patient treatment plan further includes a plurality of flow rates including at least a high flow rate which operates for time segment T1. The treatment plan further includes time segment T2, time segment T3, etc. As would be understood by those skilled in the art, where the decrease in dialysate flow rate is changed substantially continuously, such as in a linear or polynomial manner, the time period for each time segment is considered to be extremely small.

Preferably, the dialysate treatment starts at a higher dialysate flow rate, such as between 400 to 800 ml/min, and the ends at a lower flow rate between 100 to 500 ml/min. More preferably, the dialysate treatment starts at a higher dialysate flow rate between 450 to 800 ml/min and the ends at a lower flow rate between 100 to 450 ml/min. However, another patient may require a different treatment protocol. For example, in another preferred embodiment, the patient treatment plan lasts four hours and begins treatment with a dialysate flow rate of approximately 400 to 600 ml/min and decreases linearly until ending at a flow rate between 200 to 300 ml/min.

Figure 10:
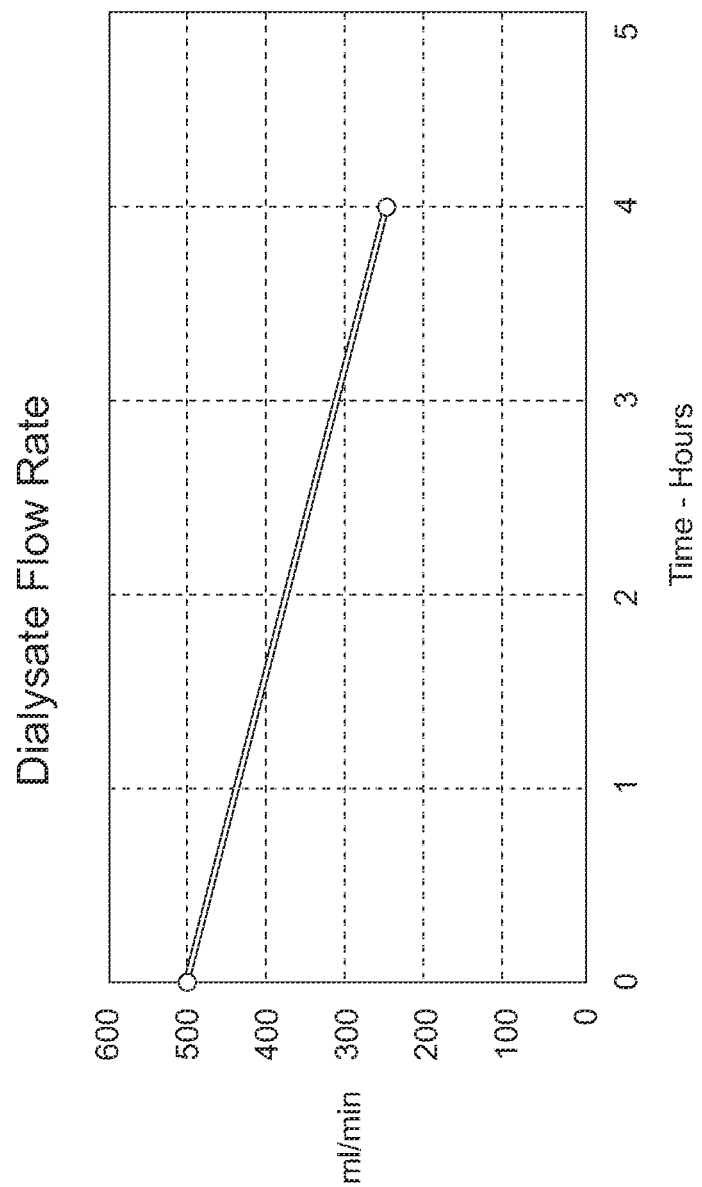
FIG. 10 is a graph illustrating a patient treatment plan with a decreasing dialysate flow rate.
Figure 11:
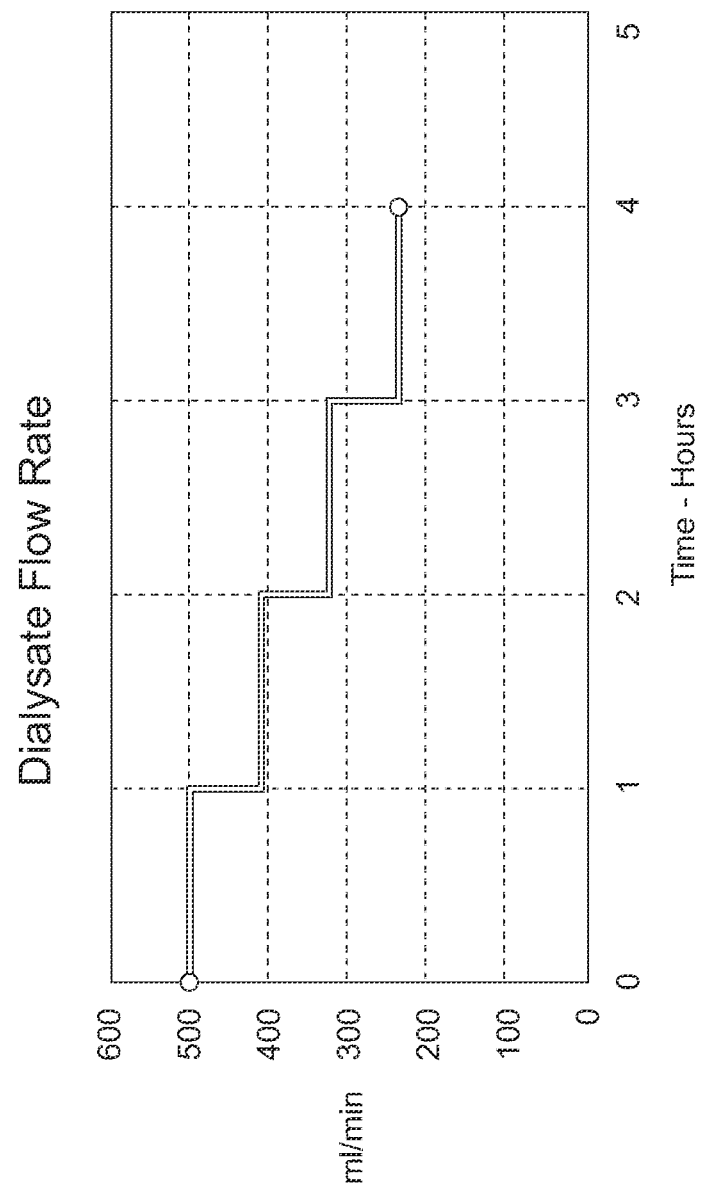
FIG. 11 is a graph illustrating a second patient treatment plan with a decreasing dialysate flow rate.
Figure 12:
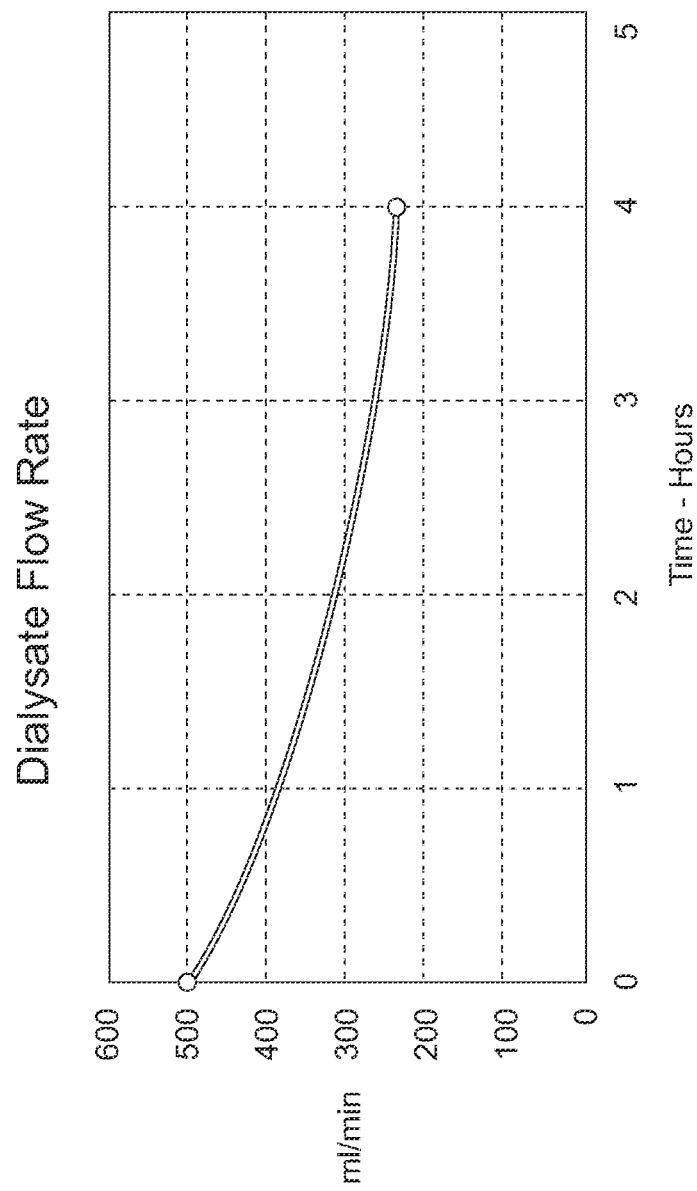
FIG. 12 is a graph illustrating a third patient treatment plan with a decreasing dialysate flow rate.
Figure 13:
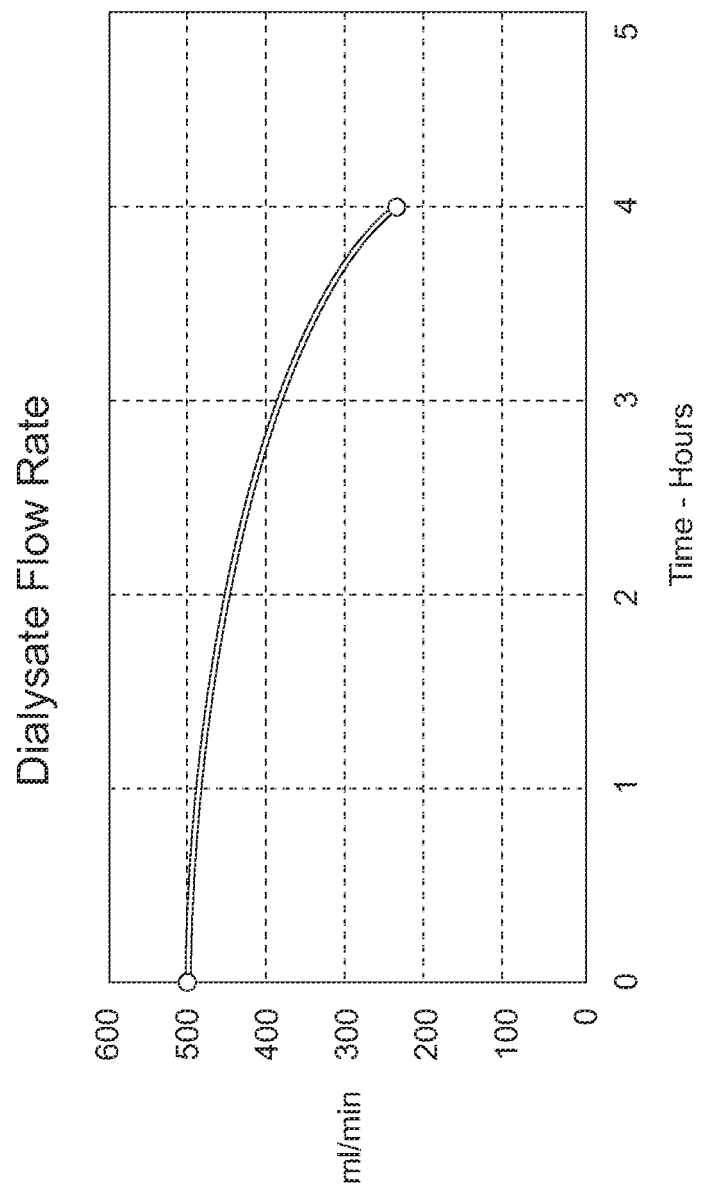
FIG. 13 is a graph illustrating a fourth patient treatment plan with a decreasing dialysate flow rate.

In the preferred embodiment illustrated in FIGS. 10-13, the patient treatment plan begins treatment with a dialysate flow rate of approximately 500 ml/min and decreases linearly for two hours until ending at a flow rate of 250 ml/min. However, the treatment protocols may be different such as decreasing linearly, as illustrated in FIG. 10, or decreasing incrementally, as illustrated in FIG. 11. For example, for the embodiment illustrated in FIG. 11, a patient is treated initially for time segment T1 of 1.0 hours at a high dialysate flow rate above 450 ml/min (illustrated at 500 ml/min), a second time segment T2 of 1.0 hours at an intermediate flow rate between 450-400 ml/min (illustrated at 417 ml/min), a third time segment T3 of 1.0 hours at an intermediate flow rate between 350-300 ml/min (illustrated at 333 ml/min); and a final time segment T4 of 1.0 hours at a low flow rate between 300-200 ml/min (illustrated at 250 ml/min). In the alternative to reducing the flow rate incrementally or linearly, the decrease in flow rate may decrease over time (−Δ), as illustrated in FIG. 12, or the decrease in flow rate may increase over time (+Δ), as illustrated in FIG. 13. For each of these examples illustrated in FIGS. 10-13, the dialysate flow rate begins at approximately 500 ml/min and decreases for four hours until ending at a flow rate of 250 ml/min. In addition to the different methods of decreasing the dialysate flow rate, the patient treatment plan's total treatment time T(total) may be determined as appropriate for each patient (such as 2-8 hours), as may the high flow rate (such as 800-400 ml/min) and low flow rate (500-200 ml/min).

To maintain proper treatment of a patient, the processor monitors all of the various sensors to ensure that the hemodialysis machine is operating efficiently and safely, and in the event that an unsafe or non-specified condition is detected, the processor corrects the deficiency or ceases further hemodialysis treatment. For example, if the venous blood line pressure sensor 9 indicates an unsafe pressure or the bubble sensor 12 detects a gaseous bubble in the venous blood line, the processor signals an alarm, the pumps are deactivated, and the pinch valves are closed to prevent further blood flow back to the patient. Similarly, if the blood leak sensor 31 detects that blood has permeated the dialyzer's semipermeable membrane, the processor signals an alarm and ceases further hemodialysis treatment.

The dialysis machine's user interface may include a keyboard or touch screen (not shown) for enabling a patient or medical personnel to input commands concerning treatment or enable a patient or medical personnel to monitor performance of the hemodialysis system. Moreover, the processor may include Wi-Fi or Bluetooth connectivity for the transfer of information or control to a remote location.

Hereinafter will be identified the various components of the preferred hemodialysis system with the numbers corresponding to the components illustrated in the Figures.

| | |
|---|---|
| 1 | Arterial tubing connection |
| 2 | Pinch valve, arterial line. Used to shut off the flow connection with the patient, in case of an identified warning state potentially harmful to the patient. |
| 3 | Bubble sensor, arterial line |
| 4 | Pressure sensor, blood pump inlet |
| 5 | Blood pump |
| 6 | Heparin supply and pump |
| 7 | Pressure sensor, dialyzer input |
| 8 | Dialyzer |
| 9 | Pressure sensor, dialyzer output |
| 10 | Bubble trap |
| 10a | Bubble trap level sensor |
| 10b | Bubble trap level sensor |
| 11 | Flow sensor, blood Circuit |

| | |
|---|---|
| 12 | Bubble sensor, venous line |
| 13 | Pinch valve, venous line |
| 14 | Venous tubing connection |
| 15 | Primary level sensor, first reservoir |
| 16 | Secondary level sensor, first reservoir |
| 17 | First reservoir which holds dialysis fluid |
| 18 | Primary level sensor, second reservoir |
| 19 | Secondary level sensor, second reservoir |
| 20 | Second reservoir which holds dialysis fluid |
| 21 | 3-way valve, reservoir outlet. |
| 22 | Temperature sensor, heater inlet. |
| 23 | Fluid heater for heating the dialysis fluid from approximately room temperature or tap temperature, up to the human body temperature of 37° C. |
| 24 | Combined conductivity and temperature sensor |
| 25 | Flow sensor, Dialysis Circuit |
| 26 | Dialysis pump, dialyzer inlet |
| 27 | Pressure sensor, Dialysis Circuit |
| 28 | Temperature sensor, dialyzer inlet |
| 29 | 3-way valve, dialyzer inlet |
| 30 | Bypass path, dialyzer |
| 31 | Blood leak detector |
| 32 | 3-way valve, dialyzer outlet |
| 33 | Dialysis pump, dialyzer outlet |
| 34 | 3-way valve, sorbent filter bypass |
| 35 | Sorbent filter bypass path |
| 36 | Sorbent filter |
| 36a | Filter |
| 37 | Ammonium ion sensor. |
| 38 | pH sensor |
| 39 | Reagent bag holds a concentrated solution of salts and ions |
| 40 | Pump, sorbent filter reinfusion. |
| 41 | Conductivity sensor, sorbent filter outlet. |
| 42 | 3-way valve, reservoir recirculation. |
| 43 | 3-way valve, reservoir drain. |
| 44 | Pump, reservoir drain. |
| 45 | Drain line connection. |
| 46 | Fresh dialysate supply |
| 47 | Pump which delivers concentrated reagents from reagent bag into fresh dialysate flow path |
| 48 | Reagent bag which holds a concentrated reagent that is introduced into fresh dialysate flow path. |
| 49 | Pump which delivers concentrated reagents from reagent bag into the water line. |
| 50 | Reagent bag which holds a concentrated reagent that will be mixed with water to form dialysis fluid. |
| 51 | Pinch valve, first reservoir inlet. |
| 52 | Pinch valve, second reservoir inlet. |
| 53 | Blood flow path |
| 54 | Dialysate flow path |
| 55 | Drain flow path |
| 56 | Fresh dialysis flow path |
| 57 | Filter flow path |
| 58 | Pump, filter flow path |
| 59 | Pressure sensor, filter flow path |
| 60 | Check valve |
| 61 | Reagents - salts |
| 62 | Pump, reagents |
| 63 | Mixer |
| 64 | Conductivity sensor |
| 65 | Reagents - bicarbonate/lactate |
| 66 | Pump, reagents |
| 67 | Mixer |
| 68 | Conductivity sensor |
| 69 | Ammonium ion sensor |
| 70 | pH sensor |
| 71 | Sorbent filter |
| 75 | Fresh dialysate |
| 76 | Contaminated dialysate |
| 77 | Control Processor |
| 78 | Control Processor Memory |
| 79 | Sample port |
| 80 | Degasser |
| 81 | Reagent level/weight sensor |
| 82 | Reagent level/weight sensor |

The hemodialysis system provides increased flexibility of treatment options based on the required frequency of dialysis, the characteristics of the patient, the availability of dialysate or water and the desired portability of the dialysis machine. For all treatments, the blood flow path 53 transports blood in a closed loop system by connecting to the arterial blood line 1 and venous blood line 14 to a patient for transporting blood from a patient to the dialyzer and back to the patient.

Figure 2:
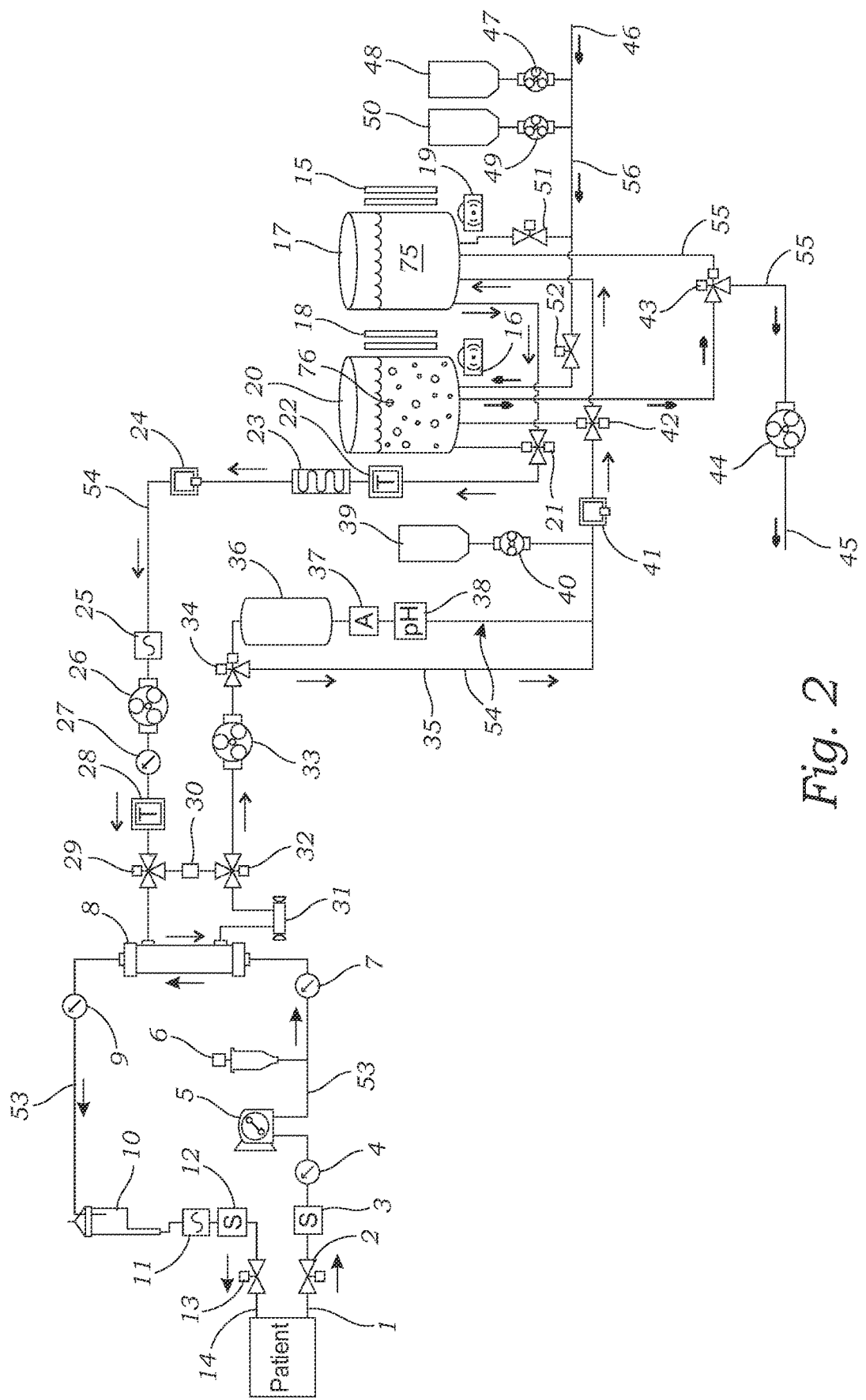
FIG. 2 is the flow chart of FIG. 1 illustrating an embodiment where dialysate avoids the filter by flowing through the bypass flow path.

With reference to FIG. 2, a first method of using the hemodialysis system does not require the use of a sorbent filter 36. Water is introduced to the machine through the fresh dialysate flow path 56 from a water supply 46 such as water supplied through reverse osmosis (RO). If needed, chemical concentrates 48 and 50 are added to the clean water using the chemical concentrate pumps 47 and 49. The mixed dialysate is then introduced to reservoirs 17 and 20. For this treatment, the dialysate 75 from a first reservoir is recirculated past the dialyzer 8 through bypass path 35 back to the same reservoir. When the volume of the reservoir has been recirculated once, the reservoir is emptied through the drain flow path 55 and the reservoir is refilled through the fresh dialysate flow path 56.

Meanwhile, while the first reservoir is being emptied and refilled, hemodialysis treatment continues using the second reservoir (17 or 20). As illustrated in FIG. 2, once the processor has determined that all dialysate has recirculated once, or determined that the dialysate is contaminated, the processor switches all pertinent valves (21, 42, 43, 51 and 52) to remove the first reservoir 20 from patient treatment, and inserts the second reservoir 17 into the dialysate flow path 54. The dialysate 75 from the second reservoir 17 is recirculated past the dialyzer 8 through bypass path 35 and back to the same reservoir 17. This switching back and forth between reservoirs 17 and 20 continues until the dialysis treatment is complete. This operation is similar, but not the same, as traditional single-pass systems because no sorbent filter is used.

Figure 3:
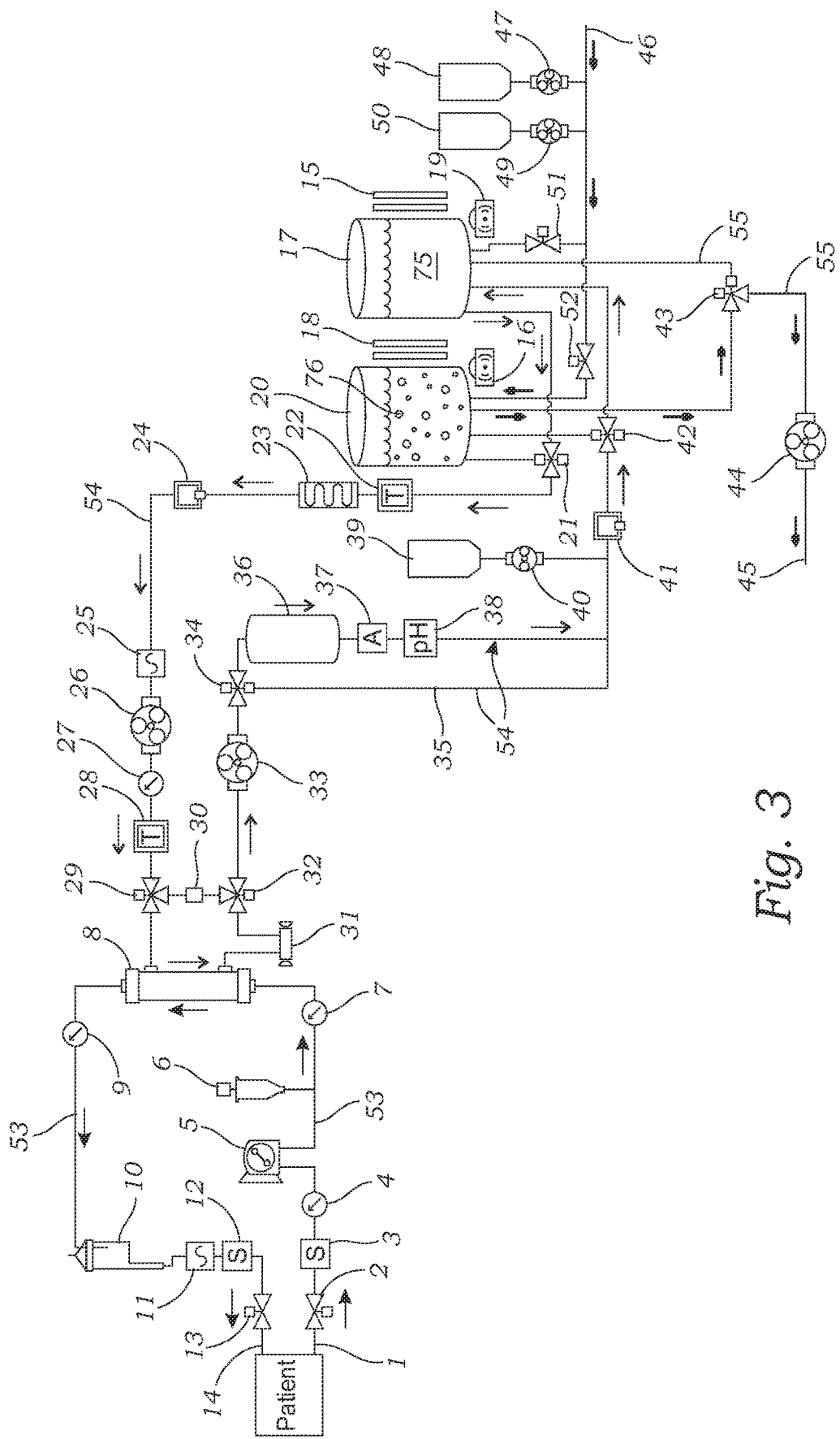
FIG. 3 is the flow chart of FIG. 1 illustrating an embodiment where dialysate flows through the filter in a closed loop dialysate flow path incorporating a first reservoir.

In a second embodiment illustrated in FIG. 3, the sorbent cartridge 36 filters the dialysate after it has passed through the dialyzer 8. To this end, the processor switches the 3-way valve 34 to incorporate the sorbent cartridge 36 into the dialysate flow path 54, and the processor switches the various valve assemblies (21, 42, 43, 51 and 52) to utilize reservoir 17 during dialysis treatment. Clean dialysate 75 is recirculated through the dialyzer 8 and sorbent cartridge 36, and thereafter the dialysate is sent back to the same reservoir 17 through the dialysate flow path 54. This recirculation continues as determined by the processor including, but not limited to, because the sorbent cartridge has been spent, or the dialysate fluid is contaminated, or ultrafiltration has resulted in the reservoir 17 becoming full and requiring that it be drained and refilled. Meanwhile, in the event the fluid in reservoir 20 is contaminated, it is drained through the drain flow path 45, and then the reservoir 20 is refilled using the fresh dialysate flow path 56.

Figure 4:
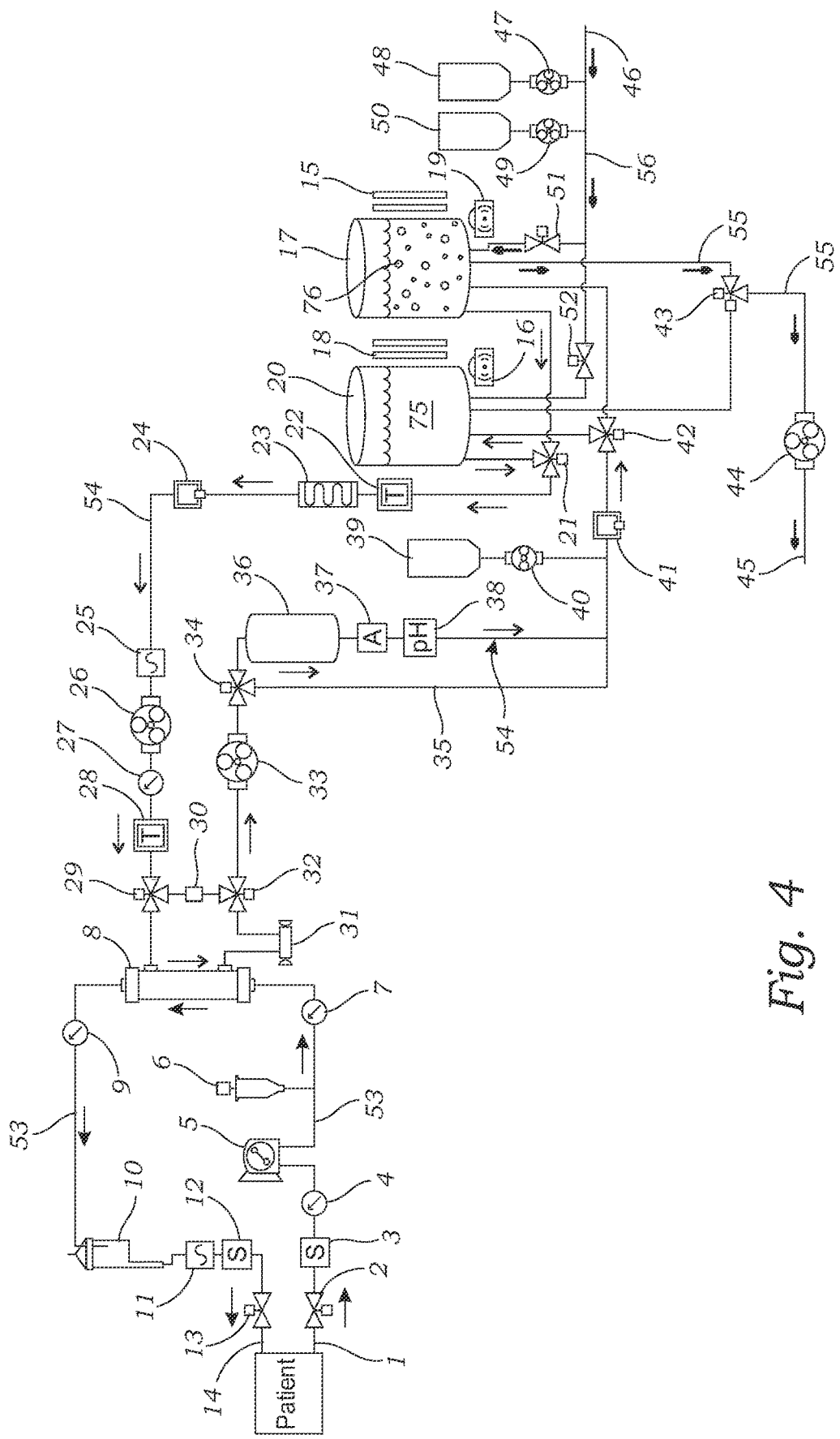
FIG. 4 is the flow chart of FIG. 1 illustrating an embodiment where dialysate flows through the filter in a closed loop dialysate flow path incorporating a second reservoir.

As illustrated in FIG. 4, once the processor has determined that continued use of reservoir 17 for dialysis treatment is not appropriate, the processor switches the various valve assemblies (21, 42, 43, 51 and 52) to remove reservoir 17 from the dialysate flow path 54, and to instead insert reservoir 20 within the dialysis flow path for dialysis treatment. Clean dialysate 75 is recirculated through the dialyzer 8 and sorbent filter 36 back to the same reservoir 20. Again, this recirculation continues using reservoir 20, as determined by the processor, until switching back to reservoir 17, or until dialysis treatment has been completed. While dialysis treatment continues using reservoir 20, contaminated fluid 76 in reservoir 17 is drained through the drain flow path. Thereafter, reservoir 17 is refilled using the fresh dialysate flow path 56. Like other treatment methods, this switching back and forth between reservoirs 17 and 20 continues until the dialysis treatment is complete.

In still an additional embodiment illustrated in FIGS. 5 and 6, hemodialysis treatment is conducted in similar manner as illustrated in FIG. 2 in which the sorbent filter 36 is not utilized within the dialysate flow path 54. Though it is possible to utilize the filter 36 within the dialysate flow path 54, for this embodiment it is preferred that the dialysate 75 be directed through the bypass path 35 so as to avoid the sorbent filter 36. During treatment, the dialysate 75 from the first reservoir is recirculated past the dialyzer 8 through bypass path 35 and directed back to the same reservoir. Even more preferably for this embodiment, the hemodialysis system does not include sorbent filter 36. Instead, with reference to FIGS. 5 and 6, the hemodialysis system includes a single sorbent filter 71 which is within a separate closed loop flow path referred to herein as the filter flow path 57. Though FIGS. 5 and 6 illustrate the hemodialysis system including two sorbent filters 36 and 71, the sorbent filter 36 within the dialysate flow path 54 is optional and does not need to be incorporated within this embodiment of the hemodialysis system.

Like the prior embodiments, dialysis treatment is implemented while switching back and forth between reservoirs 17 and 20. With reference to FIG. 5, while dialysis treatment uses the clean dialysate 75 in reservoir 17, the various valve assemblies (21, 42, 43, 51 and 52) are switched to insert the second reservoir 20 into the closed loop filter flow path 57. The contaminated water 76 is drained from the reservoir 20 through pump 58 and pressure sensor 59. Thereafter the contaminated water 76 is filtered through the sorbent filter 71. Reagents 61 and 65 may be introduced into the filter flow path using a gravity feed or pumps 62 and 66. The reagents are mixed within the mixers 63 and 67 before the now cleaned dialysate is tested for compliance by conductivity testers 64 and 68, ammonium sensor 69, and pH sensor 70. If testing shows the water is now clean, it is directed back to reservoir 20.

With reference to FIG. 6, the processor continues to monitor the output of the various sensors including those within the dialysate flow path 54. Once the water within reservoir 17 has become contaminated, it is removed from the dialysate flow path and reservoir 20 is substituted in its place by once again switching all of the pertinent valve assemblies (21, 42, 43, 51 and 52). The dialysate 75 from the second reservoir 20 is recirculated in the closed loop dialysate flow path 54 past the dialyzer 8 and directed back to the same reservoir. Meanwhile, the now contaminated water 76 in reservoir 17 is drained through pump 58 and pressure sensor 59 before being filtered through the sorbent filter 71. Again, reagents 61 and 65 may be introduced into the filter flow path 57 where the reagents are mixed within the mixers 63 and 67. The now clean dialysate is tested for compliance by conductivity testers 64 and 68, ammonium sensor 69 and pH sensor 70 before filling reservoir 17. This process of alternating reservoirs continues until the prescribed hemodialysis treatment is completed, or a fault is detected which requires that treatment be halted.

Like embodiments illustrate in FIGS. 2, 3, 5 and 6, the embodiment illustrated in FIG. 7 operates in a single pass mode. Dialysate is introduced to the machine through the fresh dialysate flow path to the reservoir 17 from a source of dialysate 46 which flows through the dialysate flow path to the dialyzer 8. Thereafter, used dialysate is then directed to a receptacle for storing waste water 55, or an effluent drain. Though not requiring the use of a sorbent filter, this single pass mode typically requires 400-600 liters of water.

Conversely, the embodiment of the hemodialysis system illustrated in FIG. 8 operates in a closed loop recirculating mode where the dialysate flows through the sorbent filter 36. Dialysate is stored in a reservoir 17 and recirculated through the dialyzer 8 and sorbent cartridge 36. Chemical concentrates 48 and 50 are added to the filtered water, as necessary. Recirculation continues as determined by the processor until treatment has completed, the sorbent cartridge has been spent, the dialysate fluid is contaminated, or ultrafiltration has resulted in the reservoir 17 becoming full and requiring that it be drained and refilled.

In closing, regarding the exemplary embodiments of the present invention as shown and described herein, it will be appreciated that a hemodialysis system is disclosed. The principles of the invention may be practiced in a number of configurations beyond those shown and described, so it is to be understood that the invention is not in any way limited by the exemplary embodiments, but is generally directed to a hemodialysis system and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the Specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present Specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

While several particular forms of the invention have been illustrated and described, it will be apparent that various modifications can be made without departing from the spirit and scope of the invention. Therefore, it is not intended that the invention be limited except by the following claims.

We claim:

1. A method of providing hemodialysis to a patient comprising steps of:
providing a system for providing the hemodialysis including an arterial blood line for connecting to a patient's artery for collecting blood from the patient, a venous blood line for connecting to a patient's vein for returning the blood to the patient, a dialyzer, a blood flow path connected to the arterial blood line and the venous blood line for transporting the blood from the patient to the dialyzer and back to the patient, a reservoir storing dialysate, a dialysate flow path connected to the reservoir and the dialyzer for transporting the dialysate from the reservoir to the dialyzer, at least one dialysate pump for pumping the dialysate through the dialysate flow path, a blood pump for pumping the blood through the blood flow path, a dialysate flow sensor in the dialysate flow path which measures a flow rate of the dialysate through the dialysate flow path, a control processor connected to the dialysate flow sensor and the at least one dialysate pump, the control processor possessing memory for storing a patient treatment plan by which the patient is treated, the patient treatment plan includes a plurality of different dialysate flow rates during a patient's treatment wherein the plurality of different dialysate flow rates decrease over a time period "T(total)" for treating the patient;
connecting the arterial blood line to the patient's artery;
connecting the venous blood line to the patient's vein;
providing hemodialysis treatment to the patient wherein the dialysate flows through the dialysate flow path at a first flow rate during a first flow period; and
providing the hemodialysis treatment to the patient wherein the dialysate flows through the dialysate flow path at a second flow rate during a second flow period which occurs after the first flow period, and the second flow rate is lower than the first flow rate.

2. The method of providing hemodialysis to a patient of claim 1 wherein the second flow rate is less than 75% of the first flow rate.

3. The method of providing hemodialysis to a patient of claim 1 wherein a flow of dialysate decreases from the first flow rate to the second flow rate in a linear manner.

4. The method of providing hemodialysis to a patient of claim 1 wherein the plurality of different dialysate flow rates decrease incrementally, and include a high flow rate and a low flow rate.

5. The method of providing hemodialysis to a patient of claim 1 wherein the plurality of different dialysate flow rates include a high flow rate between 400 to 800 ml/min and a low flow rate between 100 to 400 ml/min.

6. The method of providing hemodialysis to a patient of claim 1 wherein the first flow rate is between 400 to 800 ml/min and the first flow period is at least 0.5 hours, and the second flow rate is 100 to 400 ml/min and the second flow period is at least 0.5 hours.

7. The method of providing hemodialysis to a patient of claim 1 wherein the first flow rate is between 400 to 600 ml/min and the first flow period is at least 0.5 hours, and the second flow rate is 200 to 300 ml/min and the second flow period is at least 0.5 hours.

8. The method of providing hemodialysis to a patient of claim 1 further comprising step of:
providing the hemodialysis treatment to the patient wherein the dialysate flows through the dialysate flow path at a third flow rate during a third flow period which occurs after the first and second flow periods, and the third flow rate is lower than the first and second flow rates.

9. The method of providing hemodialysis to a patient of claim 1 wherein the first flow rate is above 450 ml/min and the first flow period is at least 0.5 hours, and the second flow rate is at least 300 ml/min and the second flow period is at least 0.5 hours, and the third flow rate is at least 250 ml/min and the third flow period is at least 0.5 hours.

10. The method of providing hemodialysis to a patient of claim 5 wherein the system for providing the hemodialysis includes a sorbent filter connected to the dialysate flow path which removes uremic toxins from the dialysate.

11. The method of providing hemodialysis to a patient of claim 1 wherein the system for providing the hemodialysis includes a sorbent filter connected to the dialysate flow path which removes uremic toxins from the dialysate.

12. The method of providing hemodialysis to a patient of claim 8 wherein the system for providing the hemodialysis includes a sorbent filter connected to the dialysate flow path which removes uremic toxins from the dialysate.

* * * * *